(12) United States Patent
Greenwood et al.

(10) Patent No.: US 6,615,827 B2
(45) Date of Patent: Sep. 9, 2003

(54) INHALATION COUNTER DEVICE

(75) Inventors: Mark H. Greenwood, Arlington Heights, IL (US); Mariann C. Straub, Winnetka, IL (US); Gabriel Rodriguez, Jr., Spring Grove, IL (US)

(73) Assignee: Sapphire Designs, Inc., Wilmette, IL (US)

( * ) Notice: Subject to any disclaimer, the term of this patent is extended or adjusted under 35 U.S.C. 154(b) by 0 days.

(21) Appl. No.: 10/119,642

(22) Filed: Apr. 10, 2002

(65) Prior Publication Data

US 2002/0189611 A1 Dec. 19, 2002

Related U.S. Application Data

(63) Continuation-in-part of application No. 09/391,169, filed on Sep. 8, 1999, now Pat. No. 6,516,799.

(51) Int. Cl.[7] .............................................. A61M 11/00
(52) U.S. Cl. ............................ 128/200.23; 128/203.12; 222/38
(58) Field of Search ....................... 128/200.23, 203.12, 128/203.23; 604/58; 222/36, 38, 25, 28, 41, 402.1–402.25; 239/71, 74; 116/308, 309

(56) References Cited

U.S. PATENT DOCUMENTS

| 165,054 A | 6/1875 | Baldwin |
| 3,119,557 A | 1/1964 | Chapman |
| 4,565,302 A | 1/1986 | Pfeiffer et al. |
| 4,817,822 A | 4/1989 | Rand et al. |
| 5,020,527 A | 6/1991 | Dessertine |
| 5,069,204 A | 12/1991 | Smith et al. |
| 5,300,042 A | 4/1994 | Kossoff et al. |
| 5,349,945 A | 9/1994 | Wass et al. |
| 5,356,012 A * | 10/1994 | Tang et al. .................. 206/534 |
| 5,411,173 A | 5/1995 | Weinstein |
| 5,421,482 A | 6/1995 | Garby et al. ................... 222/36 |
| 5,482,030 A | 1/1996 | Klein |
| 5,505,192 A | 4/1996 | Samiotes et al. |
| 5,564,414 A | 10/1996 | Walker et al. |
| 5,740,792 A | 4/1998 | Ashley et al. |
| 5,799,651 A | 9/1998 | Garby et al. ........... 128/200.23 |
| 5,829,434 A | 11/1998 | Ambrosio et al. ..... 128/203.15 |
| 6,082,358 A | 7/2000 | Scarrott et al. ........ 128/205.23 |
| 6,234,168 B1 * | 5/2001 | Bruna .................... 128/203.12 |

FOREIGN PATENT DOCUMENTS

| GB | 1 317 315 A | 5/1973 |
| GB | 2195544 A | 4/1988 |
| GB | 2348928 | 4/1999 |
| WO | WO 00/59806 | 3/2000 |

* cited by examiner

*Primary Examiner*—Weilun Lo
*Assistant Examiner*—Mital Patel
(74) *Attorney, Agent, or Firm*—Olson & Hierl, Ltd.

(57) ABSTRACT

The present invention relates to an inhalation device for dispensing a medicament from a valved dispenser. The device includes a housing having a longitudinal slot, an associated nozzle body, a cylindrical advance tube that slidably receives therein the dispenser and that has an external helically extend thread member, an advance ring that associates with the dispenser and that slidable engages the advance tube, and a level indicator. A zigzag track in either the advance tube or the advance ring, and a mating stud in the other of the ring or tube causes the advance tube to rotate when the ring is moved reciprocally when the dispenser is actuated. The level indicator device linearly indicates a remaining amount of medicament.

20 Claims, 27 Drawing Sheets

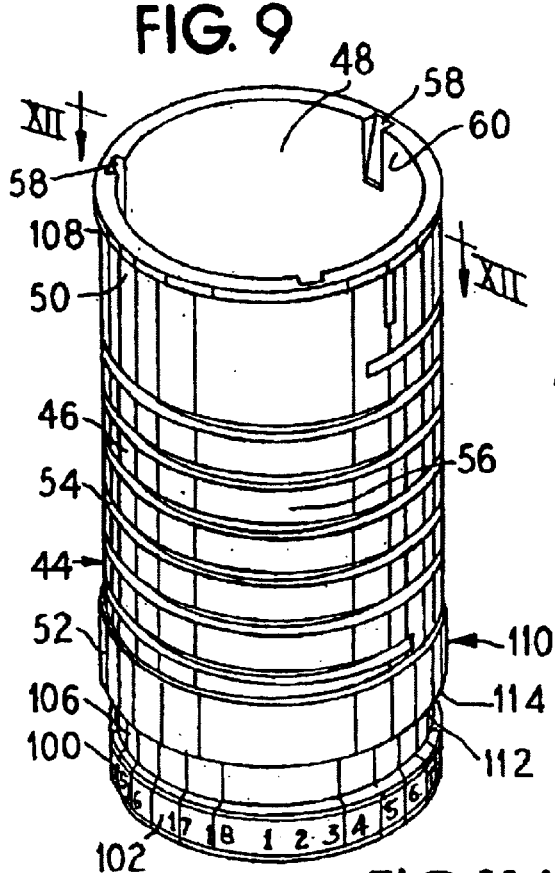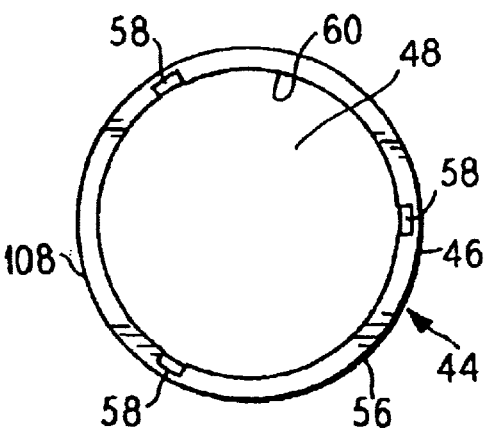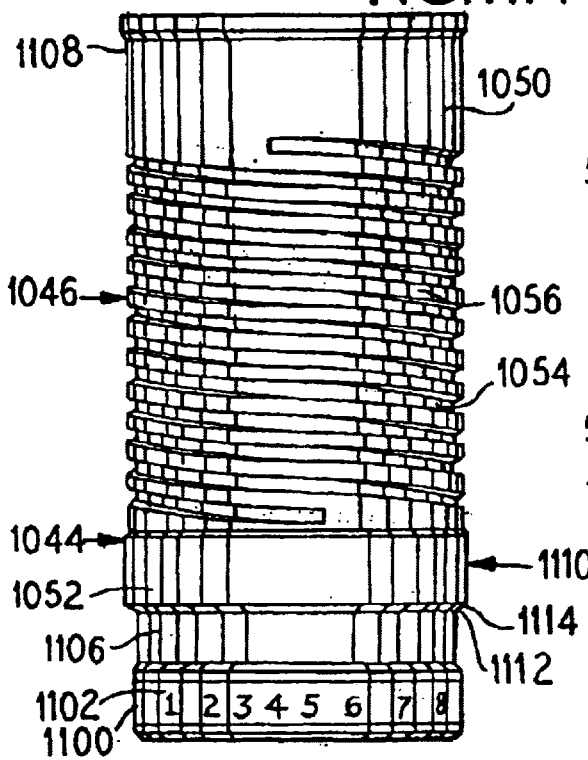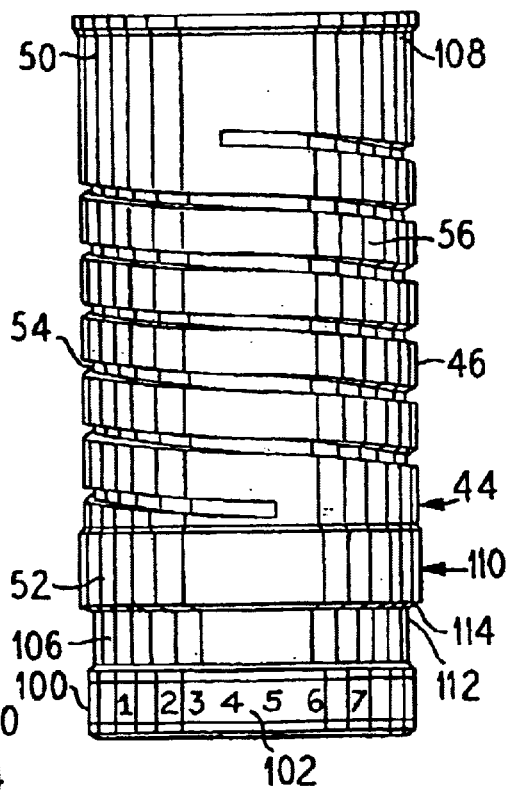

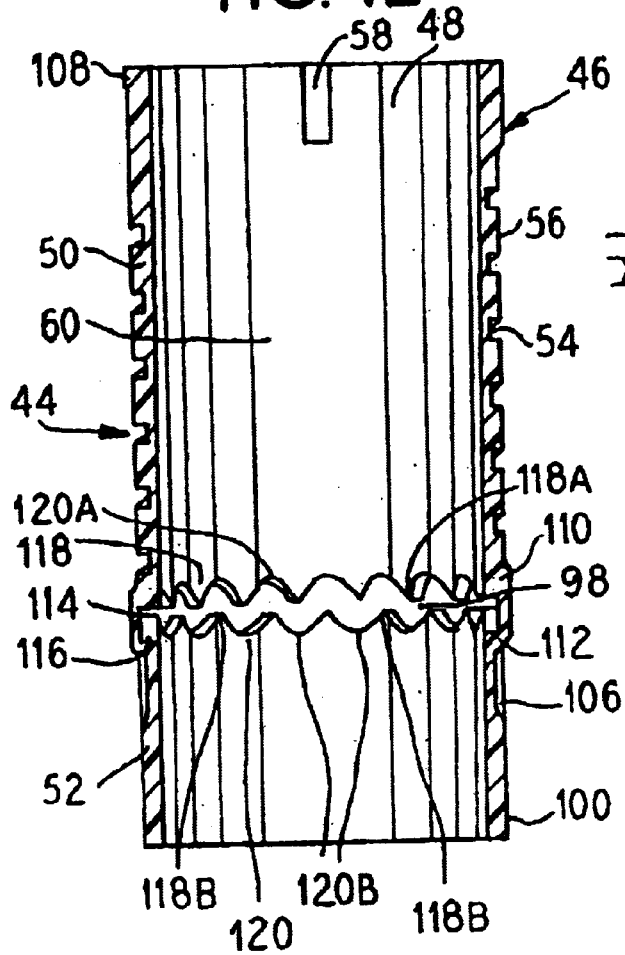
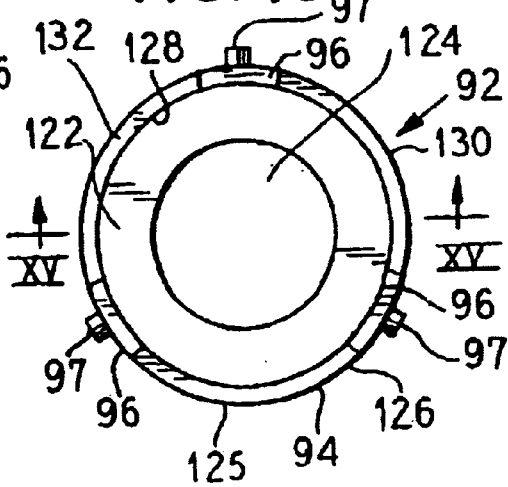
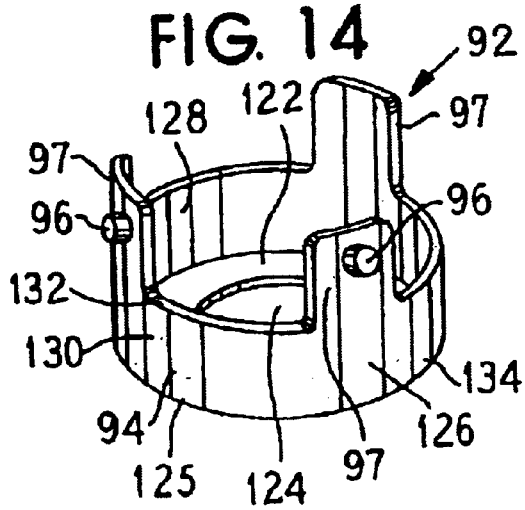
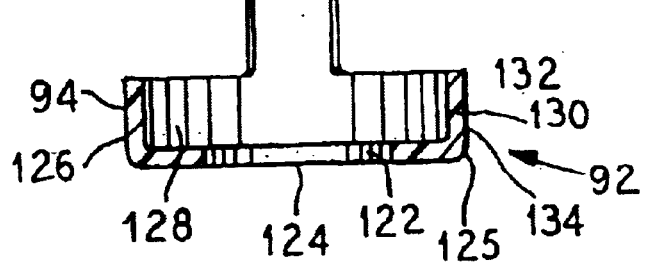

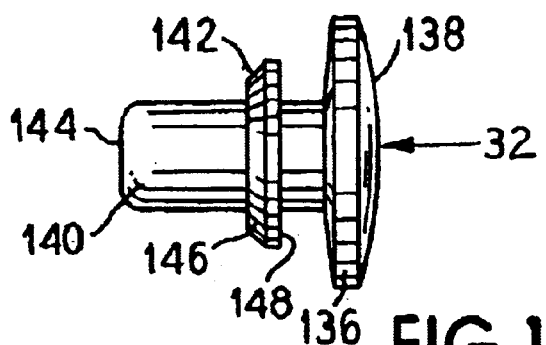
FIG. 19
FIG. 19A
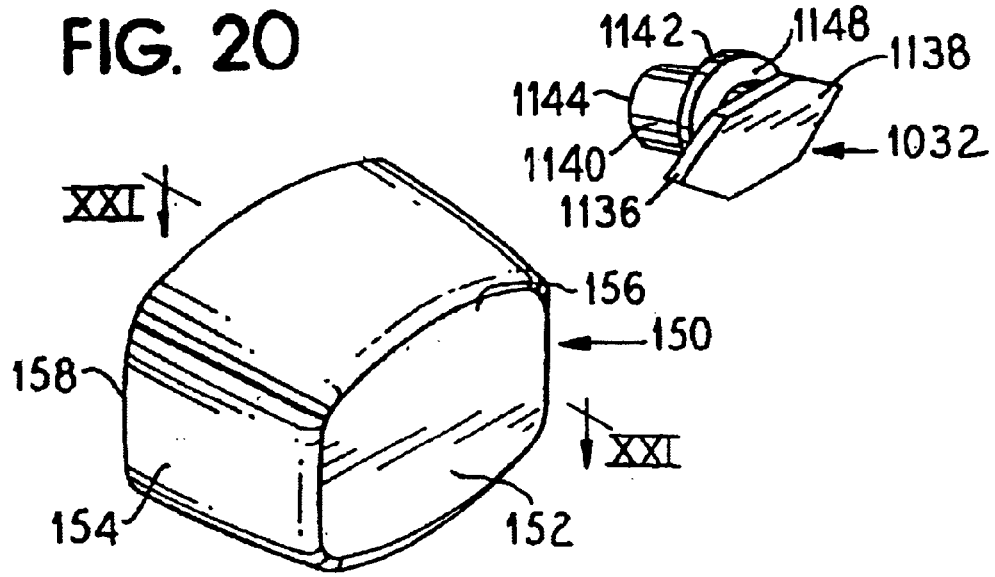
FIG. 20
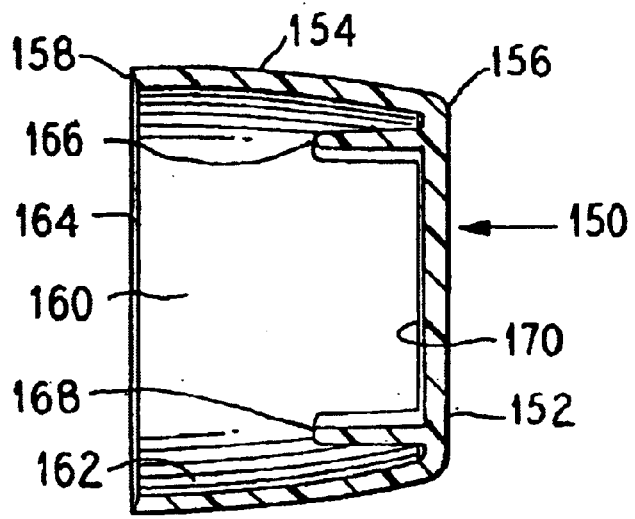
FIG. 21

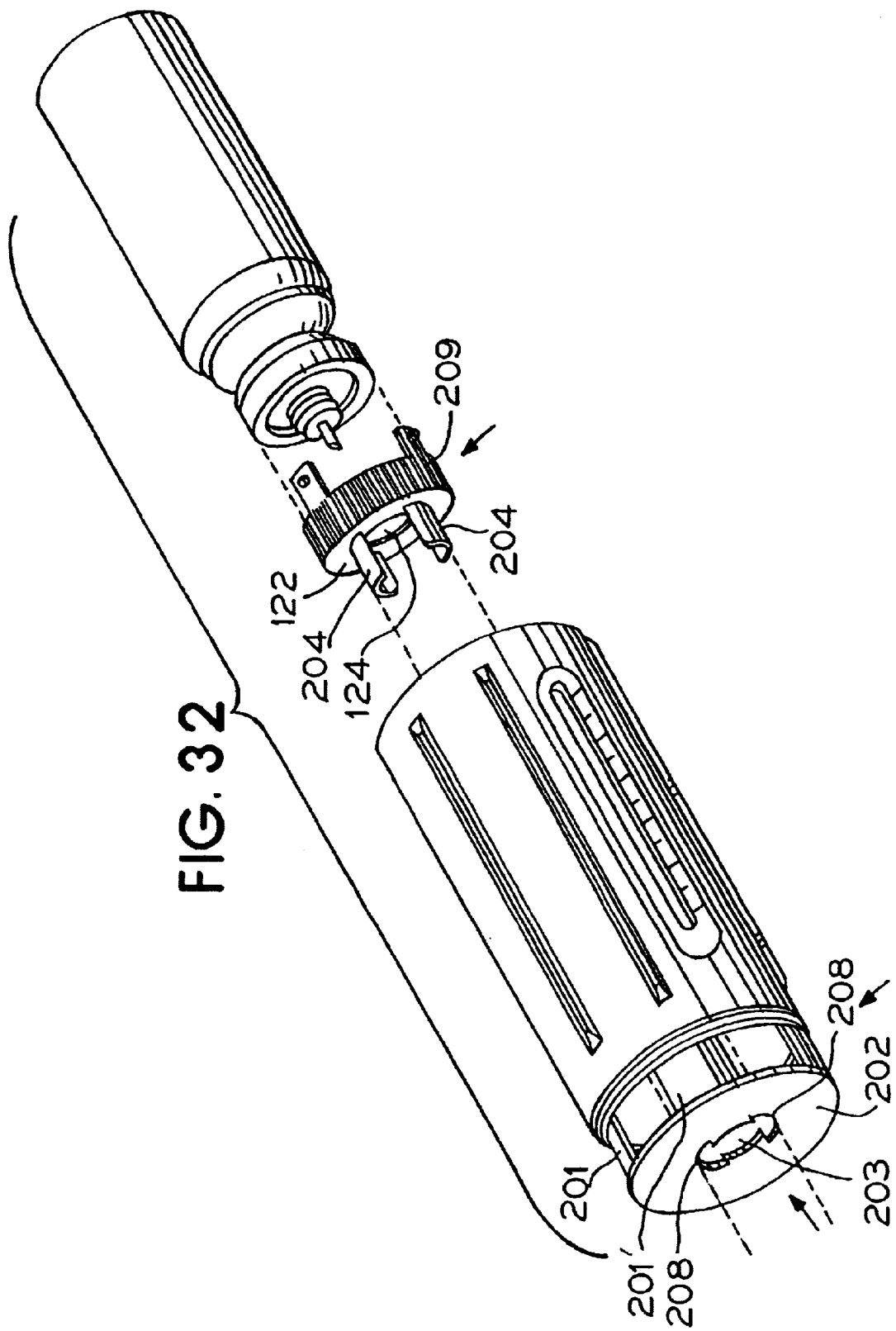

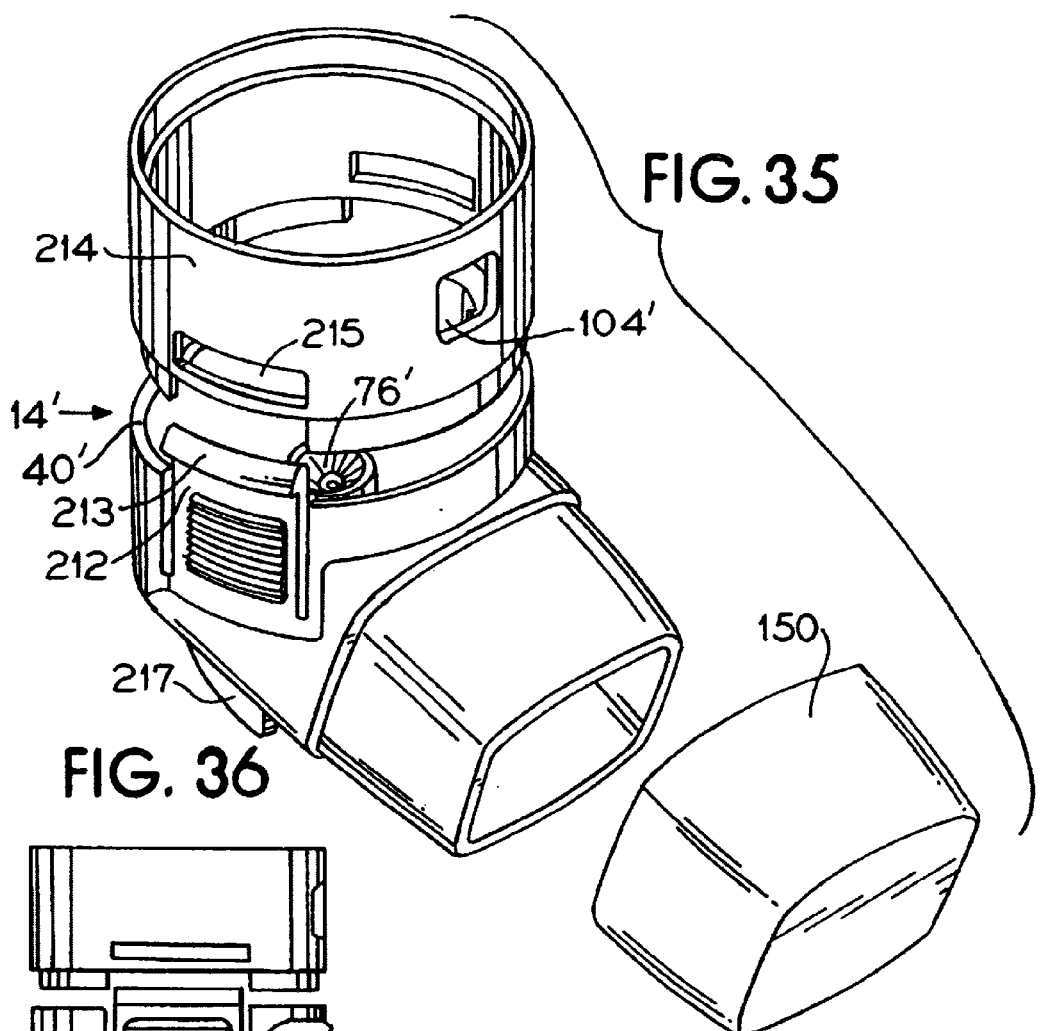
FIG. 35
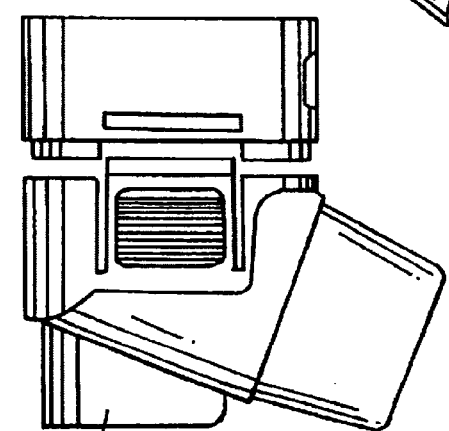
FIG. 36
FIG. 37
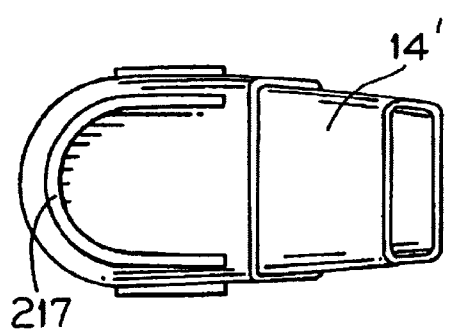
FIG. 38
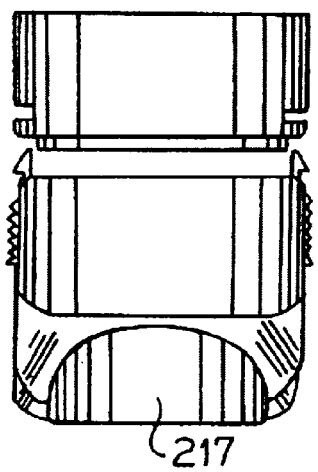

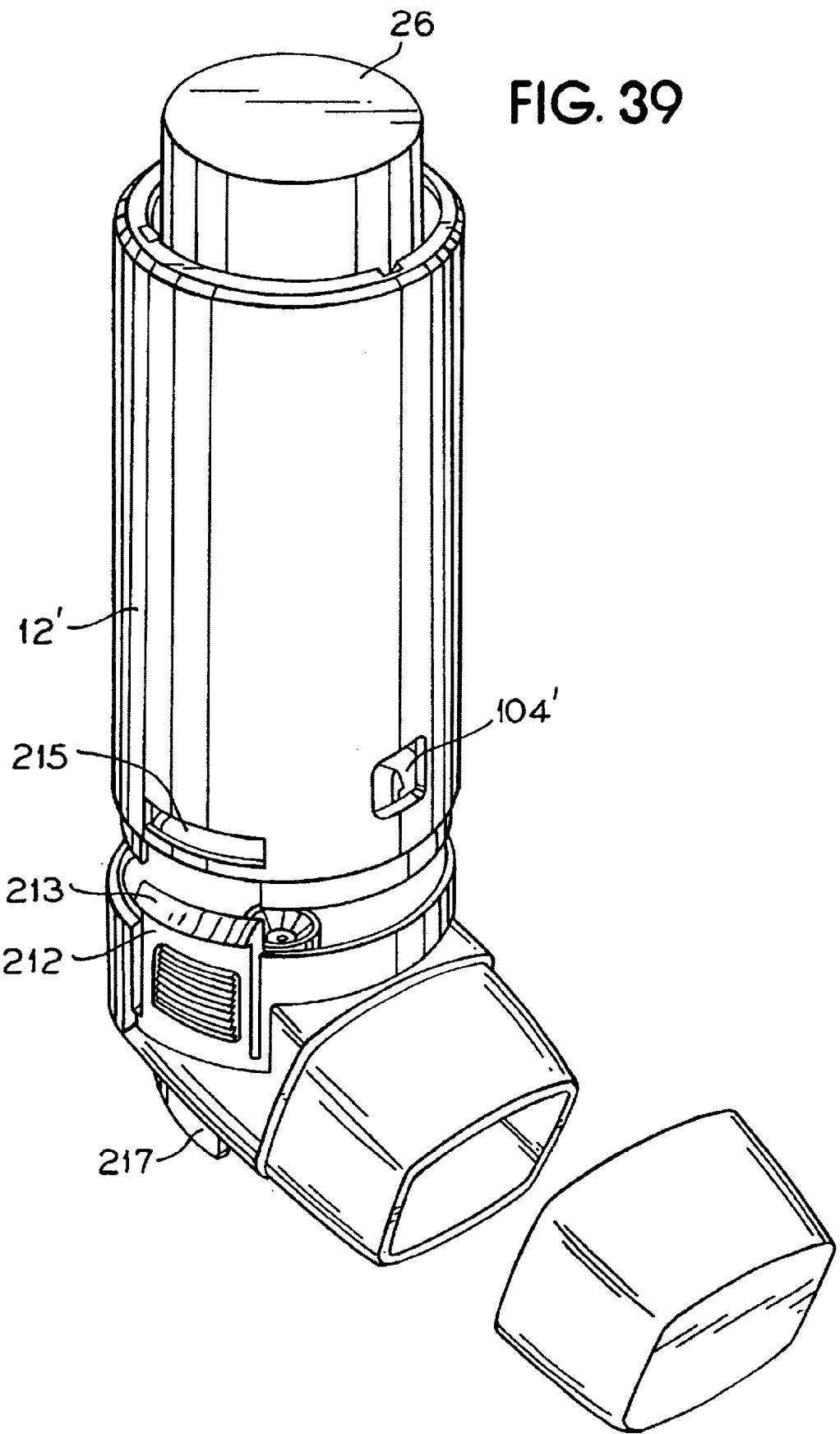

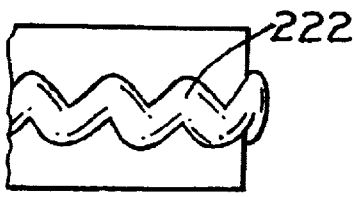
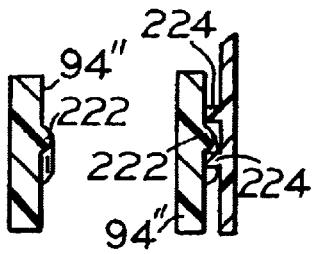
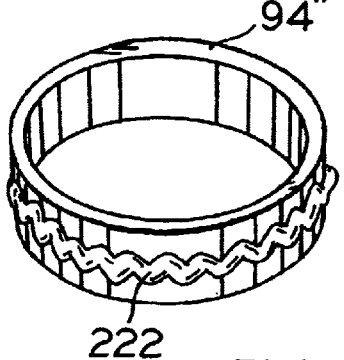
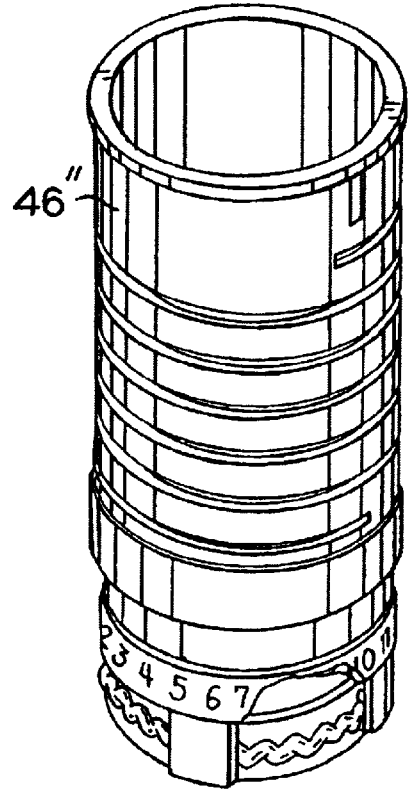
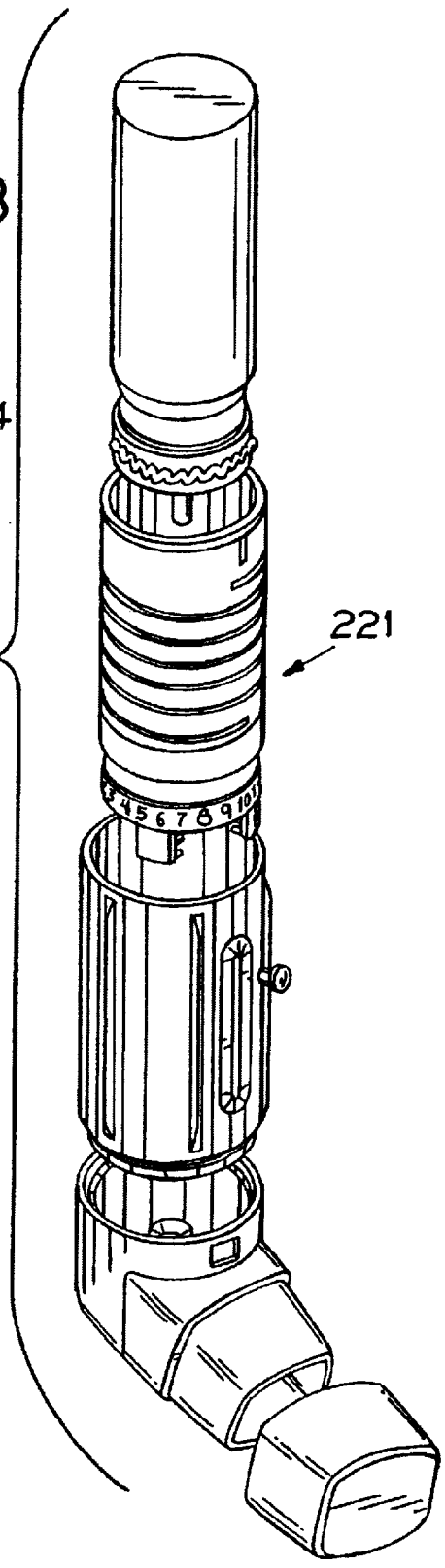

FIG. 51
FIG. 52
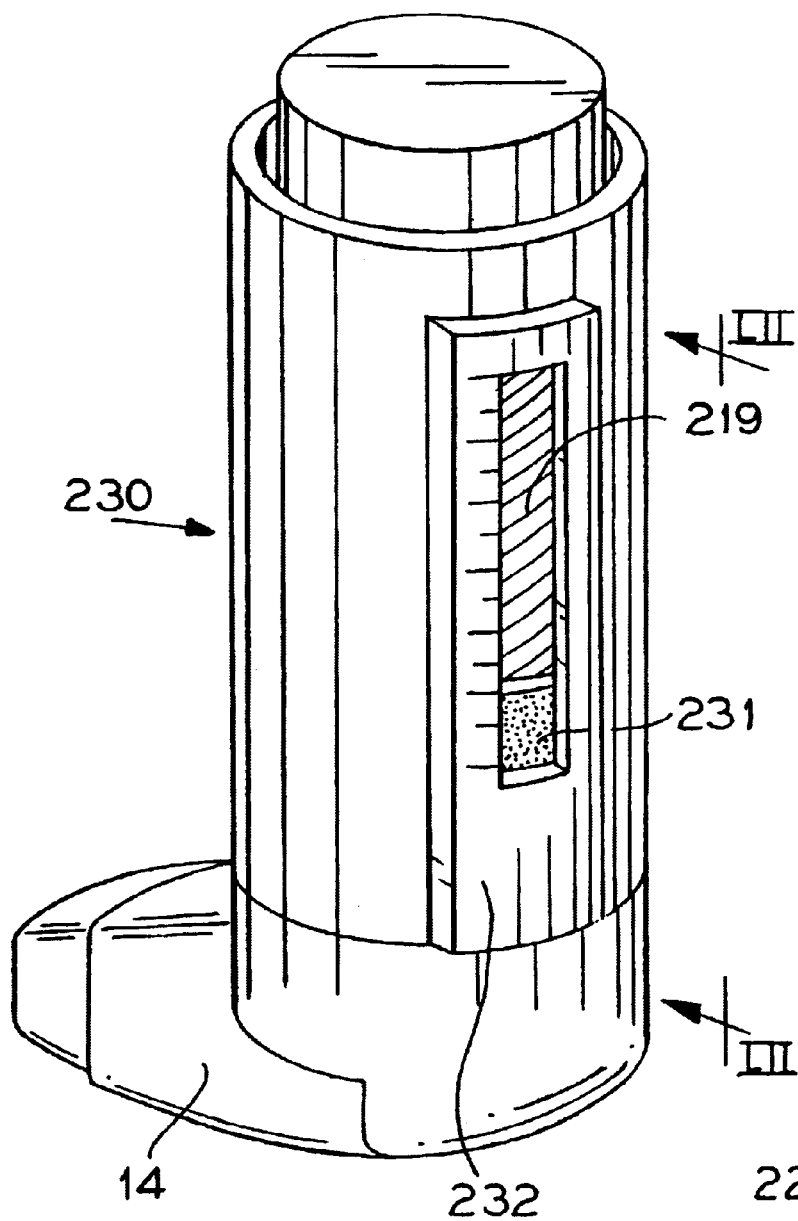
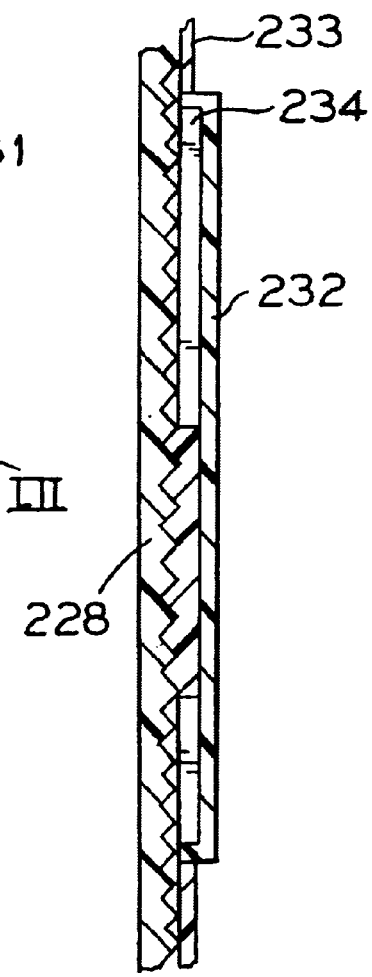

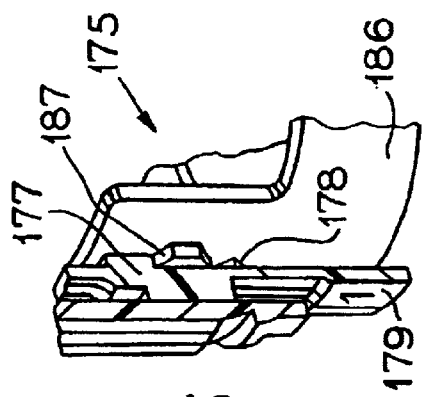
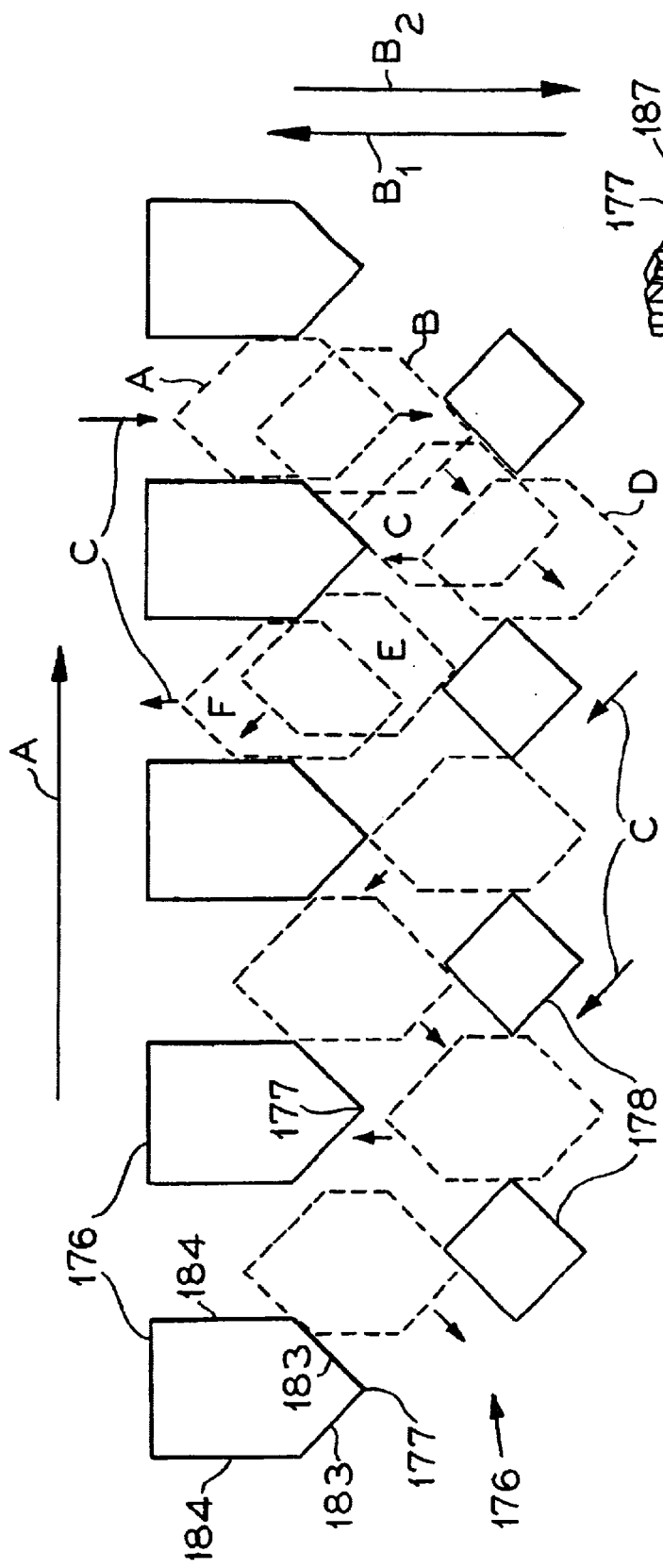
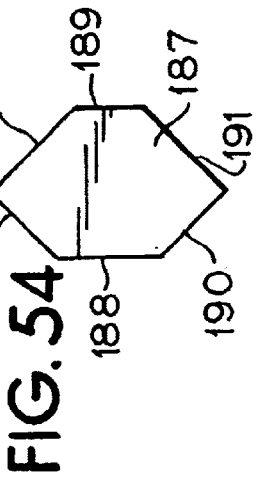

INHALATION COUNTER DEVICE

RELATED APPLICATION

This application is a continuation-in-part of U.S. patent application Ser. No. 09/391,169, filed on Sep. 8, 1999 now U.S. Pat. No. 6,516,799 issued on Feb. 11, 2003.

FIELD OF THE INVENTION

This invention relates to an improved inhalation device that indicates the amount of medicament in an associated dispenser and, optionally, the number of doses dispensed from an associated dispenser over a predetermined period.

BACKGROUND OF THE INVENTION

It is well known to treat patients with medicaments that are dispensed from an aerosol dispenser. The dispenser has become generally standardized and thus is usually in the form of a cylindrical container, usually comprised of metal, that has a proximal end and a distal end. A compression actuated, fixed dose metering and dispensing valve is axially disposed at the proximal end of the container in a constricted neck region. The valve includes an axially (relative to the container) projecting stem tube through which a single dose of aerosol medicament is dispensed in response to each valve-actuating compression of the valve.

The aerosol medication in such a container (or dispenser) can be conveniently administered to a patient by means of a prior art inhalation device that typically comprises a tubular housing or sleeve which receives and holds the dispenser and an associated nozzle from which, upon valve actuation, the medication is dispensed. The aerosol dispensers used in such inhalation devices typically are commercially readily available and are sold typically in 100 and 200 dose sizes. The outlet (or dispensing) valve member at the proximate dispenser end can be opened either by depressing the valve member while the dispenser is held stationary or by depressing the dispenser while the valve member is held stationary.

In use, an aerosol dispenser that is placed in the dispenser's tubular housing has the outlet or dispensing valve resting upon a support or valve seat in the inhalation device. The support communicates with an outlet tube (or channel) that terminates adjacently to the nozzle's mouthpiece that is usually angled relative to the dispenser housing axis. When used for dispensing medicaments, such as used, for example, in bronchodilation therapy, or the like, the housing is held by the patient in a more or less upright condition with the mouthpiece or nozzle of the inhalation device placed in the mouth of the patient. The distal end of the aerosol container is pressed towards the support to actuate the valve and dispense a dose of medicament from the container which is then inhaled by the patient.

A principal problem with prior art inhalation devices is that they provide no means by which a patient can acquire information concerning either the amount of medicament remaining in an associated dispenser or the number of doses dispensed from an associated dispenser.

Patient compliance with a doctor's instructions regarding a prescribed aerosol medication is commonly extremely important in the treatment of medical disorders. Although the rate of compliance is higher when the patient must return to the hospital or physician's office to receive the medication, most drug treatment regimens require the patient to administer the drugs at regular intervals without supervision by hospital personnel, the patient's physician or other qualified medical personnel. Obviously, the treatment of a medical disorder will be frustrated if the patient does not administer a medication as prescribed. In the past, physicians have had to rely on the patient's self-interest in his or her own well being to assure that prescribed medications (or, commonly, "drugs") are properly administered as prescribed or scheduled.

With, for example, anti-anxiety or sedative/hypnotics, such as valium and barbiturates, it is widely recognized that there is a real possibility that the patient will abuse or become dependent on the drug. Past studies have suggested that physicians should avoid the prescription of barbiturates because of the risk of dependence and the high toxicity of the drugs.

Furthermore, many such drugs have a narrow therapeutic dose range and can have severe side effects. It is well recognized that controlling the dosing of these types of drugs is important in mitigating problems with side effects. Many drugs can be extremely expensive (e.g., certain purified peptides and proteins). Controlling patient dosing of these drugs can also have economic benefits.

Dispensers, such as metered dose inhalers, nebulizers and dry powder inhalers, have been used for many years to treat pulmonary disorders such as asthma using aerosol medicaments. A metered dose inhaler typically comprises a canister pressure-fitted with a metering valve, where the canister is filled with an aerosol formulation that includes a drug dissolved or dispersed in a propellant together with a surfactant. Nebulizers are devices which include mechanical or electronic devices (e.g., a piezoelectric element) to atomize a drug suspension positioned in a containment cup. Nebulizers include an air or other gas source to deliver the atomized drug to the patient as a fine mist. Dry powder inhalers include mechanical or electronic devices to produce a fine mist or dispersion from a powdered drug composition.

Patient non-compliance while using inhalation devices has been recognized as a major medical problem. It is generally believed that most patients underdose themselves. Furthermore, over use has been observed in various studies on days following visits to the physician's office.

It is believed that, if an inhalation device were available for patient use which indicated, relative to an associated dispenser, the amount of medicament dispensed, and preferably also the number of doses administered, then a patient would be much better enabled to watch his own medication and follow a stricter dose regimen. There is a need to improve the patient's capacity for compliance with prescribed dosing schedules. There is also a need for an inhalation device which can provide some assurance that a patient is not either overdosing or underdosing a prescribed aerosol medicament, as through, for example, circumventing a dosing schedule by not inhaling the medicament.

A further disadvantage arising from use of currently available devices is that the patient cannot determine the amount of medicament in the aerosol container at any given time. In an extreme case, this could mean that the patient, possibly suffering from a severe bronchospasm and needing a dose of medicament, will find that the aerosol container will not dispense a dose because its contents have already been exhausted. There is a need for an inhalation device that avoids this problem.

Previously, in the above identified parent patent application, we have provided a new and very useful inhalation device for use in dispensing a medicament from an aerosol dispenser of the type having an axially disposed, compression actuated fixed dose metering and dispensing valve. The device provides dispenser medicament level information and dispensed dose number information.

Presently, to facilitate the use and application of such a device, we provide new and very useful improvements for association and use with the device.

SUMMARY OF THE INVENTION

The present invention relates to an improved inhalation device that is either disposable or reusable. Specifically, the present invention provides an inhalation device that, when used with a medicament dispenser, particularly a dispenser holding a pressurized medicament in aerosol form that is commercially available in a standardized multiple dose size, indicates the level of medicament in the dispenser, and, optionally also, the number of doses dispensed during a predetermined time period.

The present invention thus provides for easy and accurate dosage monitoring of the medicament, either as a single dose or multiple doses.

Examples of use of the inhalation device include delivery of a medicament to a patient's mouth, nostril, ear canal or eye. The inhalation device can be used to dispense various drugs, including beta-agonists such as albuterol (salbutamol), isoproterenol, ephedrine, epinephrine, salmeterol and terbutaline; corticosteroids such as triamcinolone acetonide, beclomethasone diproprionate, dexamethasone and aldosterone; allergic mediators such as cromcyln sodium; antibiotics; anticholinergics, and the like. Moreover, these drugs when variously formulated and charged into an aerosol dispenser can be dispensed therefrom by the inhalation device whether dissolved or dispersed in a propellant together with a surfactant, a dry powder, or other auxiliary agent.

The inhalation device includes a generally tubular housing defining a lumen that slidably receives and holds a dispenser, a nozzle body at one end of the housing, an advance tube disposed in the housing, a medicament level indicator that slidably extends through a longitudinal slot in the housing and that also slidably associates with a spiral (helical) groove defined in the advance tube, and an advance ring that includes a portion which is slidably located in the advance tube and another portion that is associated with a dispenser.

Optionally but preferably, the inhalation device includes a dose number indicator that utilizes a combination of a window that is preferably defined in the nozzle body and a sequential series of numerical markings that are arranged circumferentially about a portion of the advance tube and that are serially viewable through the window.

Preferably the nozzle body is rotatable relative to the housing, and preferably the nozzle body has an output orifice that is associatable with a replaceable and separatable end cap.

In usage of the inhalation device, the level indicator, by its externally viewable position along the longitudinal slot, indicates a remaining amount of the medicament in the dispenser, while the dose indicator, if present, indicates the number of doses dispensed.

In usage of the inhalator device, to accomplish advance of the level indicator, and of the dose indicator, if present, a radially projecting stud means that is fixed to either the advance ring or the advance tube interconnects the advance ring and the advance tube. An outer end portion of the projecting stud means rests in a serrated (or zigzag) groove defined, correspondingly and reciprocally, in either the advance tube or the advance ring. When the valve of a dispenser that is associated with the inhalation device is actuated, the advance ring moves longitudinally and reciprocatingly. The projecting stud means exerts a camming force against side edge portions of the zigzag groove, and the advance tube is caused to rotate relative to the housing. Concurrently, the level indicator slidably advances both along the helical groove and also along the longitudinal groove. Also concurrently, if the dose indicator is present, a next succeeding dose number moves into viewability in the window.

When the window is in the nozzle body, and the nozzle body is rotatable relative to the housing, dose indicator device can be reset to zero by such rotation so that the number of doses taken in any predetermined time period can be monitored.

One feature of the present invention is that the inhalation device is provided with auxiliary key means for preventing rotation of the advance ring during actuations of the dispenser valve yet allowing longitudinal reciprocal movements of the advance ring.

Another feature of the present invention is that the inhalation device is provided with auxiliary means for accommodating operation of the inhalation device when the medicament level indicator has reached the limit of display capability.

Another feature of the present invention is that the inhalation device is provided with alternative structures and arrangements for the advance ring and the cooperating advance tube.

Another feature of the present invention is that the inhalation device is provided with alternative structures and arrangements for the nozzle.

Numerous other advantages and features of the present invention will become readily apparent from the following detailed description and from the accompanying drawings.

BRIEF DESCRIPTION OF THE DRAWINGS

In the drawings:

FIG. 9 is a perspective view of the advance tube of the FIG. 1 embodiment removed from the housing and other components and showing the sequential series of numerical markings that are arranged circumferentially about the advance tube;

FIG. 10 is a top plan view of the FIG. 9 advance tube;

FIG. 11 is a side elevational view of the FIG. 9 advance tube;

FIG. 11A is a side elevational view of an alternate embodiment of the advance tube of FIGS. 9 and 11;

FIG. 12 is a longitudinal cross sectional view of the FIG. 9 advance tube taken substantially along the line XII—XII of FIG. 9 and showing the serrated groove portion defining the upper and lower portions of the advance tube;

FIG. 13 is a top plan view of the advance ring of the FIG. 1 embodiment removed from the other components;;

FIG. 14 is a perspective view of the advance ring of FIG. 13;

FIG. 15 is a transverse cross sectional view of the FIG. 13 advance tube taken substantially along the line XV—XV of FIG. 13;

FIG. 19 is a side elevational view of the pointer (or level indicator) of the FIG. 1 embodiment removed from the housing and other components;

FIG. 19A is a perspective view of an alternate embodiment of the pointer of FIG. 19;

FIG. 20 is a perspective view of the replaceable cap that removably engages the nozzle of the FIG. 1 embodiment and is removable therefrom; and FIG. 21 is a longitudinal cross sectional view of the FIG. 20 cap substantially along the line XXI—XXI of FIG. 20.

FIG. 30A is a fragmentary perspective view of the combination of advance tube and advance ring in the embodiment of FIG. 30;

FIG. 32 is another view similar to FIG. 30, but showing another alternative arrangement for keying the advance ring to an extended portion of the housing;

FIG. 35 is an exploded perspective view of an alternative nozzle structure;

FIG. 36 is a side elevational view of the FIG. 35 nozzle structure;

FIG. 37 is a back end elevational view of the FIG. 35 nozzle structure;

FIG. 38 is a bottom plan view of the FIG. 35 nozzle structure;

FIG. 39 is a perspective view side of an alternative embodiment of an inventive inhalation device;

FIG. 43 is an exploded perspective view of an alternative embodiment of an inventive inhalation device;

FIG. 44 is a perspective view of the advance ring of the FIG. 43 embodiment;

FIG. 45 is a perspective view of the advance tube of the FIG. 43 embodiment shown in combination with the FIG. 44 advance ring, some parts thereof being broken away;

FIG. 46 shows diagrammatically and illustratively an enlarged section of the serrated ridge on the outside surface of the advance ring in a laid flat orientation showing the unique dimensions of the ridge as a pathway that is followed by a pair of guide skids of the advance tube when the valve member of an associated dispenser is actuated by compression;

FIG. 47 is a vertical sectional view through a side of the FIG. 44 advance ring;

FIG. 48 is a fragmentary vertical sectional view through the FIG. 44 advance ring and the FIG. 45 advance tube in interengaged relationship;

FIG. 51 is a perspective view of the FIG. 49 embodiment;

FIG. 52 is a fragmentary vertical sectional view taken longitudinally along the line LII—LII in FIG. 51 through the housing, the advance ring, and the level indicator leaf of the FIG. 48 embodiment;

FIG. 53 is similar to FIG. 23 but illustrating an alternative embodiment of the inhalation device;

FIG. 54 is a plan view of one pin member employed in the FIG. 53 embodiment; and FIG. 55 is a fragmentary vertical sectional view of a portion of the FIG. 53 embodiment in the region of interengagement between pin member and post and diamond members.

DETAILED DESCRIPTION

Figure 1:
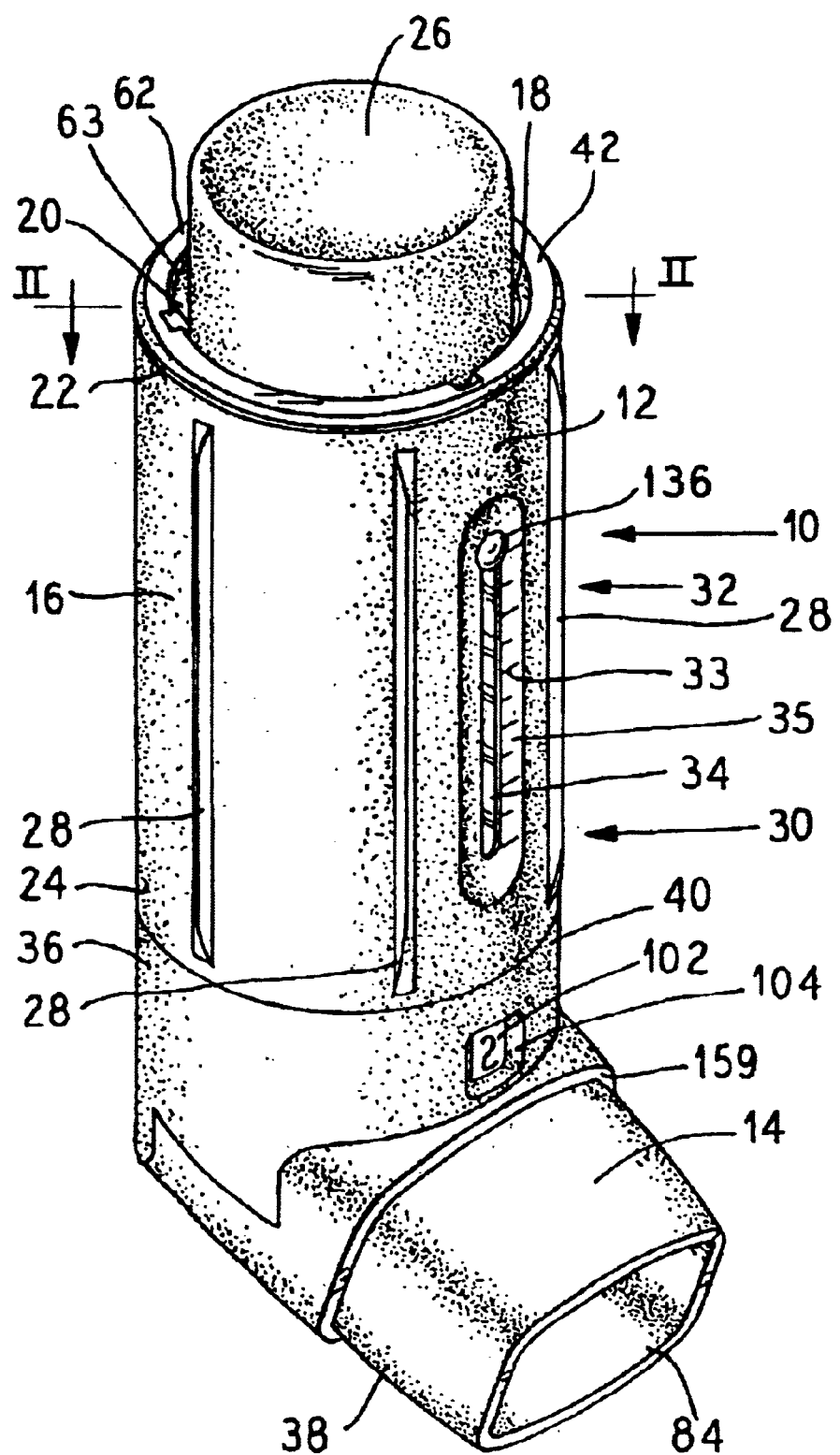
FIG. 1 is a perspective view of one embodiment of the inventive inhalation device.

While this invention can be embodied in many different forms, there are shown in the drawings and described in detail, presently preferred embodiments of the present invention. The present disclosure is an exemplification of the principles of the invention and is not intended to limit the invention to the embodiments illustrated.

Figure 8:
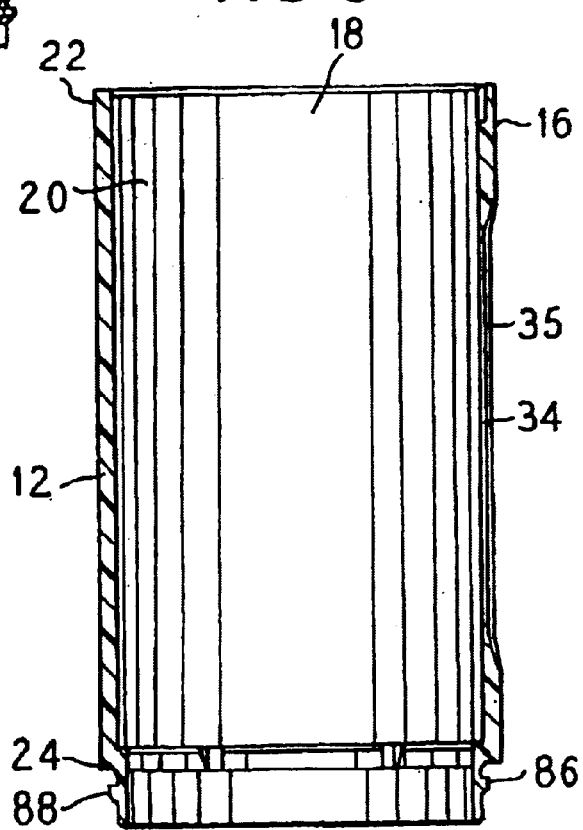
FIG. 8 is a longitudinal cross sectional view of the FIG. 5 housing inhalation device taken substantially along the line VIII—VIII of FIG. 5.

Turning to FIG. 1, a perspective view of an embodiment of the inventive inhalation device for dispensing a medicament, generally designated 10, is shown. The inhalation device 10 includes a housing 12 and a nozzle 14 that is generally L-shaped when viewed from the side. Standing alone, the housing 12 has a generally tubular shape when viewed from the side (see FIGS. 2, 6 and 8) and includes an outer surface 16 and an inner surface 18 that defines a lumen 20.

Housing 12 is formed with proximal and distal ends 22 and 24, respectively, and is adapted to receive an advance tube 46 and a medicament dispenser 26 (see FIGS. 1 and 2) in lumen 20. A plurality of ribs or fins 28 is integrally formed with, and extend from, outer surface 16. In the embodiment 10 (see FIG. 1), six fins 28 are provided in circumferentially equally spaced relationship about housing 12, although other numbers and configurations of fins (or ribs) 28 and the like are contemplated. Fins 28 provide a non-slip surface for gripping the housing 12 in addition to adding to the overall appearance.

The inhalation device embodiment 10 includes a level indicator device 30 operably associated with the housing 12 for indicating a remaining amount of the medicament in the dispenser 26. The level indicator device 30 includes a level display device 32 that is operably associated with the advance tube 46 and the housing 12. A longitudinal slot 34 is defined through the housing 12 parallel to a longitudinal axis thereof and communicates with the lumen 20. The level display device 32 is movably and slidably disposed in slot 34 and is operably associated with the advance tube 46 by a snap fit or the like. In addition, the housing 12 further defines a depression or concave engaging portion 35 in the outer surface 16 about and in proximity to the slot 34. Concave engaging portion 35 allows the level indicator device 32 to move in a linear fashion along the slot 34 without interference from the user. In the embodiment 10, slot 35 includes markings or indicia 33 to indicate the amount of medicament remaining in the dispenser 26.

While one longitudinal slot 34, one concave engaging portion 35 and one level display device 32 are shown, other arrangements are contemplated. For example, two slots 34, each formed with a concave engaging portion 35, could be defined, each one on an opposing side of the housing 12 with a display device 32 operably associated with each slot. In this manner, the medicament level could be determined from opposing sides of the device 10.

FIG. 1 further shows that the nozzle 14, whose output opening 84 is intended for insertion into the mouth of a user, includes upper and lower portions 36 and 38, and is in operable communication with the housing 12 and the lumen 20. While the nozzle 14 is designed for insertion into the mouth, it is contemplated that it could be reconfigured and used with or inserted into the user's eye, nostril, ear or any other orifice. As shown, the upper portion 36 has a proximal end 40 that is snap-fitted to the distal end 24 of the housing 12, so that the nozzle 14 is in fluid communication with the lumen 20. Although a snap-fit is described, any means for rotably connecting the nozzle 14 to the housing 12 is contemplated, including an airtight friction fit, reciprocally spaced threads formed on the housing 12 and nozzle 14, screws, pins, etc.

Figure 2:
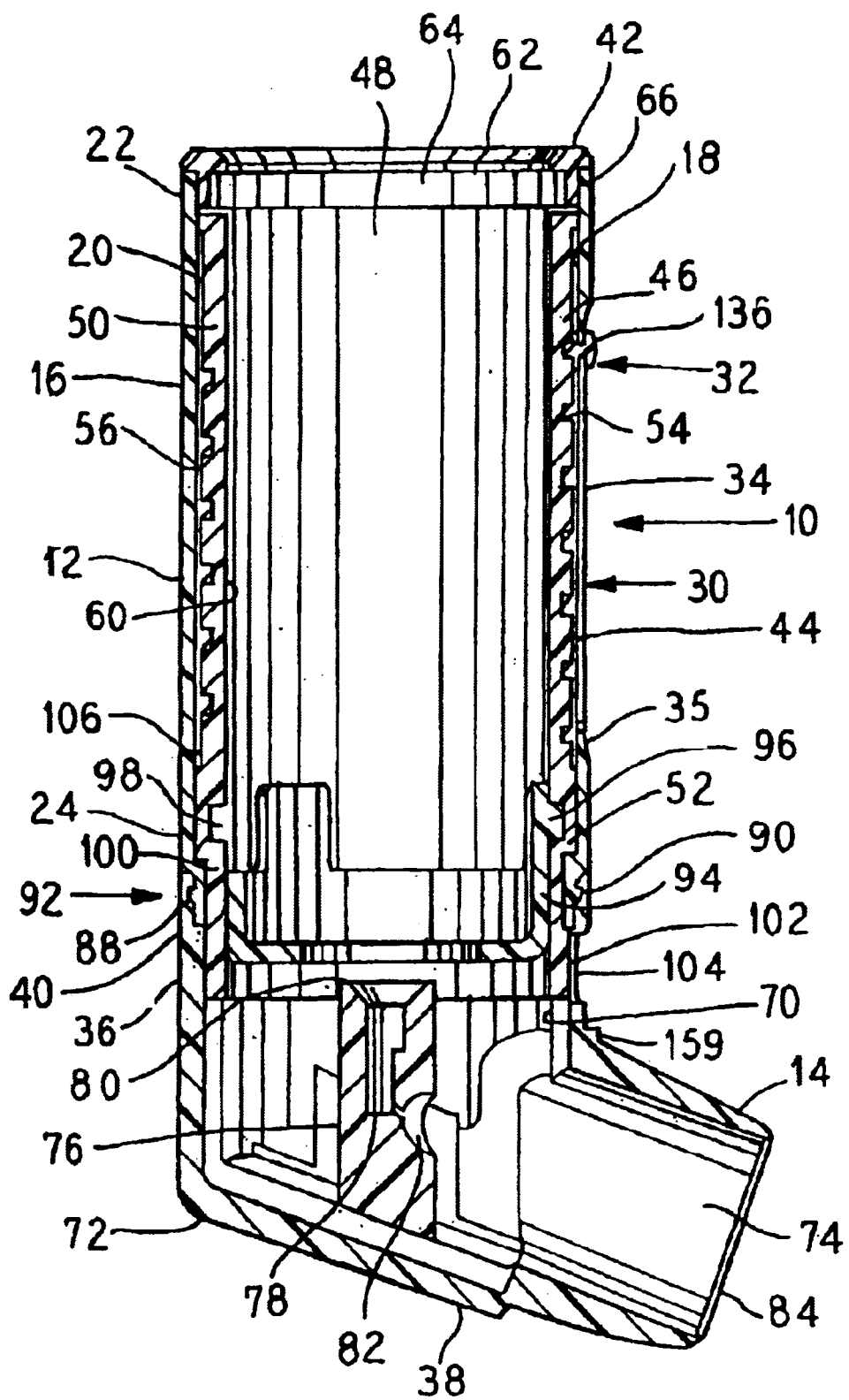
FIG. 2 is a longitudinal cross sectional view of the FIG. 1 inhalation device taken substantially along the line II—II of FIG. 1.
Figure 3:
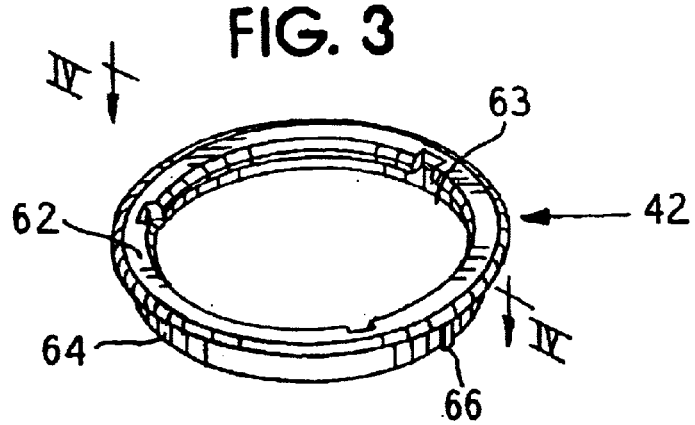
FIG. 3 is a perspective view of the top ring member of the FIG. 1 inhalation device.
Figure 4:
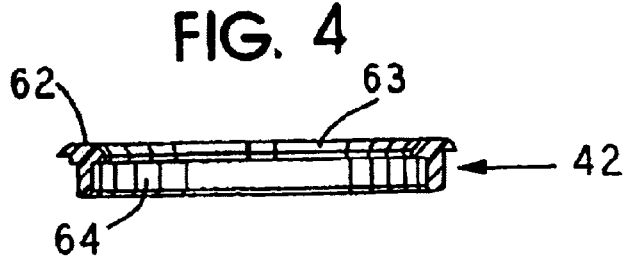
FIG. 4 is a diametrical cross-sectional view of the FIG. 3 top ring member taken substantially along the line IV—IV of FIG. 3.

FIG. 2 shows a side elevational view of the inhalation device 10 is partial cross-section. FIG. 2 shows that the device 10 includes a top member or ring 42 (see FIGS. 3 and 4) operably associated with the proximal end 22 of the housing 12. In one contemplated embodiment, top member 42 is operably associated with the housing 12, the level indicator device 30 and the medicament dispenser 26, thereby to prevent the level indicator device 30 and/or the medicament dispenser 26 from becoming unintentionally or accidentally separated from the housing 12.

FIG. 2 further shows that the level indicator device 30 includes an advance device 44 movably disposed within the lumen 20 of housing 12. In the preferred embodiment 10, the advance device 44 includes the advance tube 46 which defines a tube lumen 48. The advance tube 46 is rotatably disposed within the lumen 20 of housing 12.

At least one helically wound groove 54 (see FIGS. 9 and 11) is defined in the tubular outer surface 56 of the advance tube 46 and is operably associated with the level display device 32. Conveniently, the level display device 32 is snap-fitted into the helical groove 54 through the longitudinal slot 34. It is contemplated that a medicament dispenser 26 that is functionally associatable with the device 10 could be sold in a multiplicity of doses. Typically, a medicament dispenser 26 is contemporarily available either with 100 or 200 doses, although other dose amounts are contemplated. It is therefore contemplated that the level indicator device 30 of the present invention should accommodate a dispenser 26 containing such different dose units (sizes). The spiral angle, linear length and/or spacing of the helical groove 54 could vary depending on the dispenser 26 dose size, i.e. 100 or 200 doses. Furthermore, while only one helically wound groove 54 is shown, two or more grooves are contemplated.

In addition, it is contemplated that advance tube 46 includes at least one linear, longitudinally extending notch or groove 58 defined in the inner surface 60 of advance tube 46 and in fluid communication with tube lumen 48. In embodiment 10 (see FIGS. 1 and 9), three elongated grooves 58 are defined in equally spaced relationship about inner surface 60 along or parallel to the longitudinal axis of the advance tube 56. Each longitudinal groove 58 is preferably operably associatable with portions of an advance ring 94 as discussed below.

Top member 42 has a circular shape and is preferably formed of a surgical metal material or rigid plastic suitable for sterilization and reuse or disposal. Top member 42 is preferably formed with both a ring portion 62 with a skirt portion 64 that generally downwardly depends from ring portion 62. Top member defines an central aperture 63 and the skirt portion 64 is formed with at least one generally outwardly extending flange member 66 (see FIG. 3). Top member 42 is operably associated with the housing 12 so that ring portion 62 is in contact with and rests upon the proximal end 22, while the skirt portion 64 extends into the lumen 20. Preferably, extending member 66 operably engages at least one housing groove 68 (see FIG. 5) defined in the inner surface 18, so that the medicament dispenser 26 is securably movably mounted in the lumen 20 and extends through the aperture 63. In embodiment 10, the top member 42 is operably associated with both the advance device 44 and the medicament dispenser 26, so that the dispenser 26 is mounted for longitudinal reciprocal motions while the advance tube 46 is mounted for rotational movements in the lumen 20. Furthermore, top member 42 assures that dispenser 26 is properly centered in lumen 48.

Provision is further made for removably connecting the nozzle 14 to the housing 12, so that the nozzle 14 is in rotatable, removable, and operable communication with the lumen 20. FIG. 2 shows that the nozzle 14 includes nozzle inner and outer surfaces 70 and 72, respectively, and includes a nozzle lumen 74 defined by nozzle inner surface 70 so that nozzle lumen 74 is in fluid communication with the lumen 20. While only one nozzle lumen 74 is shown, a plurality thereof are contemplated that are substantially co-axially aligned with each other and all in fluid communication with the lumen 20. Further, a plurality of flat panels 75 are preferably defined about the circumference of inner surface 70 which operably engage a corresponding number of flat panels 87 formed on housing 12. These panels coact to permit the nozzle 14 to be rotated in incremental steps and to provide a tactilly sensible perception by one rotating the nozzle 14, as desired for purposes of aligning the nozzle window or display port 104 with individual numbers (that indicate dose number) 102 imprinted on the lower portion of the advance tube 46, as those skilled in the art will readily appreciate.

As shown in FIG. 1, medicament dispenser 26 may be inserted into the lumen 20 preferably by inserting the dispenser 26 into tube lumen 48 so that the distal end of the dispenser 26 preferably protrudes somewhat from the proximal end 22 of the housing 12. Spacer ribs (not shown) may be provided on advance tube 46 inner surface portions 60 so that the medicament dispenser 26 is held uniformly spaced therefrom. As shown, for example, in FIGS. 16–18, a support or valve seat 76 is provided in the nozzle 14 which has a passageway 78 defined therein that is in fluid communication with the lumen 20, so that the medicament dispenser 26 can be supported by and located therein. In embodiment 10, support 76 defines a first opening 80 and second opening 82 with the passageway 78 being in fluid communication with and extending between both the first and second openings 80 and 82. Furthermore, the first opening 80 is defined in proximity to and in fluid communication with the lumen 20, while the second opening 82 is in proximity to and in fluid communication with the nozzle lumen 74.

When the inhalation device 10 is used with a medicament dispenser 26, the protruding proximal portion including the dispenser 26 outlet valve member (not shown) is inserted into the first opening 80 and the passageway 78, so that the dispenser 26 is supported by the support 76. The outlet valve member of the medicament dispenser 26 can be actuated by depressing the distal end of the dispenser 26 relative to the housing 12 to an extent sufficient to move the dispenser 26 body longitudinally relative to the housing 12 and the nozzle 14 and against the support 76, and thereby open the dose dispensing valve in the medicament dispenser 26 so that a premeasured dose of medicament is discharged. One dose of medicament is discharged each time the dispenser 26 is fully depressed. The medicament is discharged from the dispenser 26 valve into the passageway 78 through second opening 82 and into the nozzle lumen 74 from which it can be inhaled or otherwise delivered to the user through the nozzle opening 84.

Figure 5:
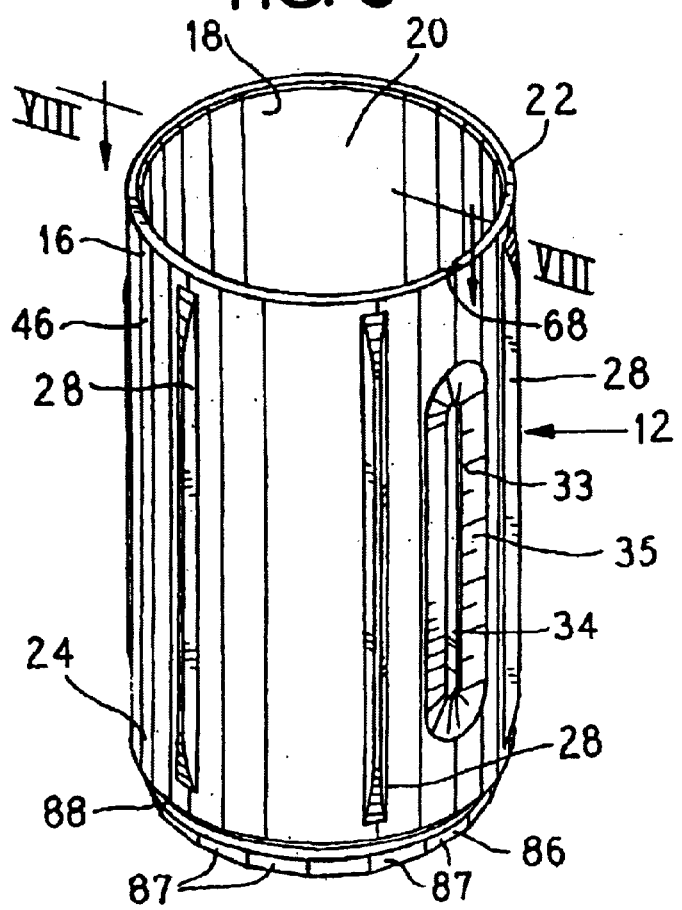
FIG. 5 is a perspective view of the housing of the FIG. 1 embodiment with the top member, nozzle and other components removed.
Figure 6:
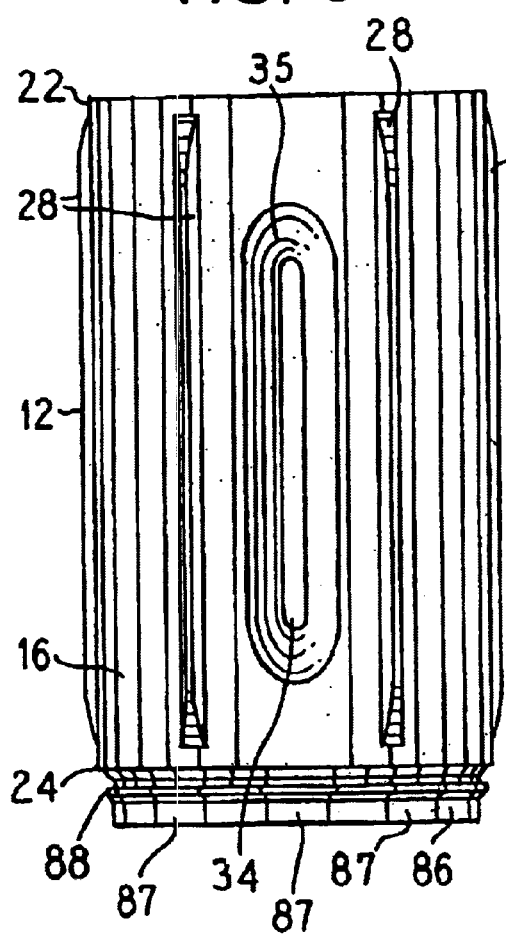
FIG. 6 is a side elevational view of the housing of FIG. 5.
Figure 7:
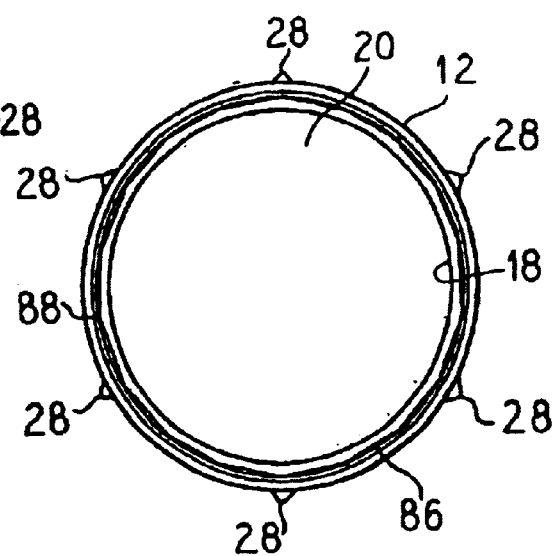
FIG. 7 is a bottom plan view of the housing of FIG. 6 showing the distal end of the housing extended ring portion.

An integrally formed, extended ring portion 86 at the distal end 24 of the housing 12 and has a plurality of flat panels 87 formed on circumferentially extending surfaces thereof (see FIGS. 5 and 6). Preferably, the extended ring portion 86 is utilized to secure the nozzle 14 to the housing 12 in a snap-fit manner, so that the nozzle 14 is in fluid communication with the lumen 20. Extended ring portion 86 is formed with at least one connecting point, preferably a lip 88 projecting generally radially outwardly from the extended ring portion 86, and extending around the circumference thereof. While one lip 88 is shown, two or more lips 88 or even a plurality of generally radially outwardly extending nubs spaced about extended ring portion 86 are contemplated.

Correspondingly, at least one connecting point is formed on the nozzle 14. At least one annular groove 90 (see FIGS. 16 and 18) is defined by the nozzle 14 inner surface 70, the groove 90 extending around the inner circumference of nozzle proximal end 40. Groove 90 is in spaced relationship to, and positionally aligned with, lip 88, and so frictionally accommodates the lip 88. The groove 90 is defined to receive the lip 88 of the housing 12 so that the groove 90 and lip 88 act in concert to secure the nozzle 14 to the housing 12 in an air-tight, snap-type friction fit. Again, while this snap-type friction fit is preferred, other securing means are contemplated for rotably securing nozzle 14 to housing 12.

In embodiment 10, the extended ring portion 86 and nozzle 14 illustratively each include eighteen panels 87 and 75, respectively, that cooperate to provide a slight friction therebetween that allows the nozzle 14 to rotate about the housing 12, similar to that of a watch bezel. Rotating the nozzle 14 relative to the housing 12 allows the dose indicator device to be reset at the end of each predetermined period, whether daily, weekly, monthly, etc. The slight friction between panels 75 and 87 prevents such reset from occurring accidentally; thus, the operable engagement of panels 75 and 87 requires that the dose indicator device be deliberately reset by the user.

As shown in FIG. 2, an advance member 92 is disposed in the lumen 20 of housing 12 in operable communication with the advance device 44. In embodiment 10, the advance member 92 comprises an advance ring 94 having at least one and preferably a plurality, here illustratively three, projecting stud members, 96 that each project radially from ring 94 and that are integral therewith. The ring 94 and the stud members 96 are disposed within tube lumen 48. A serrated portion (or zigzag groove) 98 (see FIG. 12) is defined in the inner surface 60 of the advance tube 46 in proximity to the distal end of tube 46 lower portion 52, and the projecting members 96 are operably associated with the serrated groove 98.

FIGS. 5–8 show various views of housing 12 with the top member 42 and the nozzle 14 removed, and include a perspective view, a side elevational view, a bottom plan view and a side elevational view in cross-section. Housing 12 has a generally rectangular, tubular shape when viewed from the side (see FIGS. 6 and 8) and a circular shape when viewed from the bottom (see FIG. 7). In one preferred embodiment, housing 12 is formed of surgical metal material or rigid plastic suitable for sterilization and reuse or disposal.

As shown in FIGS. 5–8, the housing 12 has an outer surface 16 and inner surface 18 that defines the lumen 20. Housing 12 is formed with proximal and distal ends 22 and 24, respectively, and is adapted for receiving the medicament dispenser 26 (not shown but see FIG. 1) in the lumen 20. The housing 12 is configured for removably and rotationally receiving the advance tube 46 in the lumen 20.

Operation of the level indicator device 30, which can be considered to include the advance device 44 that is disposed within the lumen 20 of housing 12, is illustrated by FIGS. 9–11. In embodiment 10, advance tube 46 defines the tube lumen 48, includes upper and lower tube portions 50 and 52, and is rotatably disposed within the lumen 20. An indented portion 106 that is defined by outer surface 56 of tube 46 in proximity to distal end 100 of tube 46 lower portion 52, is provided and is in addition to the helically extending groove 54 defined in outer surface 56.

In embodiment 10, each longitudinal notch or groove 58 extends only part way along the inner surface 60 of tube 46, and the notches or grooves 58 each provide a lead in for inserting advance ring 94 into the lumen 48 during embodiment 10 assembly. The advance ring 94 is initially positioned in tube lumen 48 so that each of the projecting members 96 on ring 94 operably engage a different notch or groove 58. In one disposable embodiment, advance ring 94 is fixedly connected to the dispenser 26, being held in place by gluing, bonding, crimping, a press-fit or the like. However, a reusable embodiment is preferred wherein advance ring 94 is preliminarily frictionally associated with the dispenser 26 and is, after usage of the dispenser 26, detachable therefrom for reuse with a different dispenser 26. Preferably, the advance ring 94 slidably advances after association with a dispenser 26 in the tube lumen 48 in a linear and longitudinal fashion until the projecting member(s) 96 of the ring 94 operably engage(s) the serrated groove 98.

In embodiment 10, illustratively, the advance tube 46 is formed of two parts, tube upper and lower portions 50 and 52, respectively, which are operably associated with each other (see FIG. 12). Distal end 110 of tube upper portion 50 is operably associated with the proximal end 112 of tube lower portion 52. In embodiment 10, extended portion 114 that is formed at the distal end 110 engages, or rests upon, the shoulder 116 that is formed at the proximal end 112. Other means and methods of operably associating tube 46 upper and lower portions 50 and 52 are contemplated, including threads, gluing, bonding and the like. An advance tube 46 can be formed as a unitary piece by molding or the like, if desired.

Figure 22:
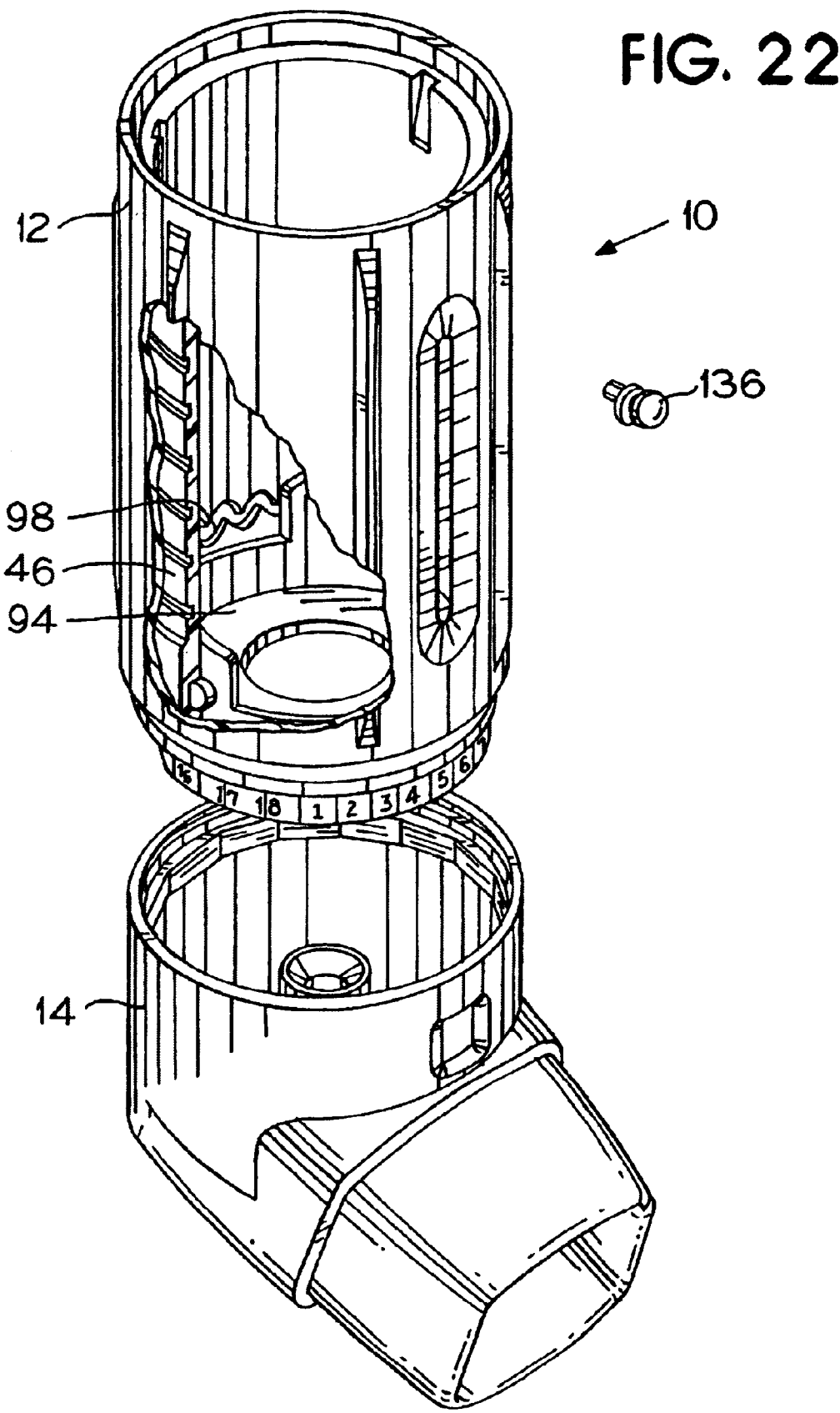
FIG. 22 is an exploded view of the FIG. 1 embodiment, some parts thereof broken away and some parts thereof shown in section.

The interrelationship between the housing 12, the nozzle 14, the advance tube 46 and the advance ring 94 is illustrated in FIG. 22. As further explained below, when, in one cycle of operation, the advance ring 94 is moved longitudinally downwards and upwards reciprocatorily relative to the housing 12 and the advance tube 46 during operation of the assembled device 10, the advance tube 46 incrementally rotates in one direction a predetermined amount. The same rotation of the advance tube 46 moves level display device 32 in the longitudinal slot 34 and advances the numerical indicia 102 viewable through the window or display port 104 in nozzle 14.

Distal and proximal ends 110 and 112 of advance tube 46 define the serrated groove portion 98 in embodiment 10. The projecting members 96 of the advance member 94 operably engage serrated groove 98 and the teeth 118 defined therealong (the teeth being generally designated as 118 and including proximal and distal teeth 118A and 118B, respectively). Grooves 120 are defined between the teeth 118 (the grooves 120 being generally designated as 120 and including proximal and distal grooves 120A and 120B, respectively). Downward pressure on the dispenser 26 moves the associated advance ring 94 downwards and causes the projecting members 96 to move longitudinally downwards and into and along adjacent edge portions of the teeth 118, and to press downwardly and against adjacent edge portions of the teeth 118 and the grooves 120. Releasing the downward pressure on the dispenser 26 after a medication dose has been dispensed through the dispenser 26 valve, causes the dispenser 26 to move upwards, the upward force being provided by the spring bias of the dispenser 26 valve, and the advance member 92 and the projecting members 96 move upwardly to the tip of the next tooth 118 in the series of teeth 118 and into the next groove 120 in the series of grooves 120, in a rachet-like fashion. As the projecting members 96 engage the grooves 120 and the teeth 118, they cause the advance tube 46 to rotate in the lumen 20. Thus, in embodiment 10, applying and releasing longitudinal pressure (force) to the dispenser 26 and associated advance ring 94 causes advance tube 46 to rotatably move in one chosen direction in a sort of rachet-like fashion.

Closer inspection of FIG. 12 reveals that the proximal and distal series of teeth 118A and 118B are offset circumferentially relative to each other. Thus, proximal teeth 118A are in a longitudinally spaced relationship relative to the distal grooves 120B, while distal teeth 118B are longitudinally spaced relationship relative to the proximal grooves 120A. Downward pressure on the advance ring 94 causes the stud members 96 to move longitudinally into, and press downwardly on, the distal groove 120B defined between teeth 118B. Releasing the pressure on advance ring 94 causes the projecting members 96 to move upwardly, and to hit (engage) the proximal tooth 118A just slightly off-center, i.e., just off the tip of the proximal tooth 118A, and then move into and towards the top of the next proximal groove 120A in the series, causing the advance tube 46 to rotate in the lumen 20.

The serrated groove portion 98 provides an advancing track or groove for regulating the rotational the advance and position of tube 46. As indicated, the serrated groove 98 is defined in, and extends circumferentially about, the inside surface 60 of the advance tube 46.

Figure 23:
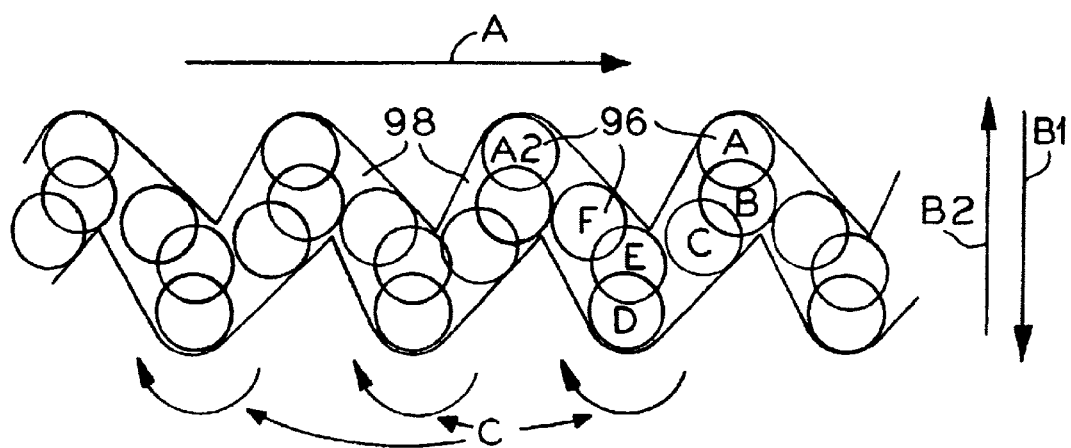
FIG. 23 shows diagrammatically and illustratively an enlarged section of the serrated groove on the inside surface of the advance tube in a laid flat orientation showing the unique dimensions of the groove and the pathway in the serrated portion that is followed by a projecting pin member of the advance ring when the valve member of an associated dispenser is actuated by compression.
Figure 26:
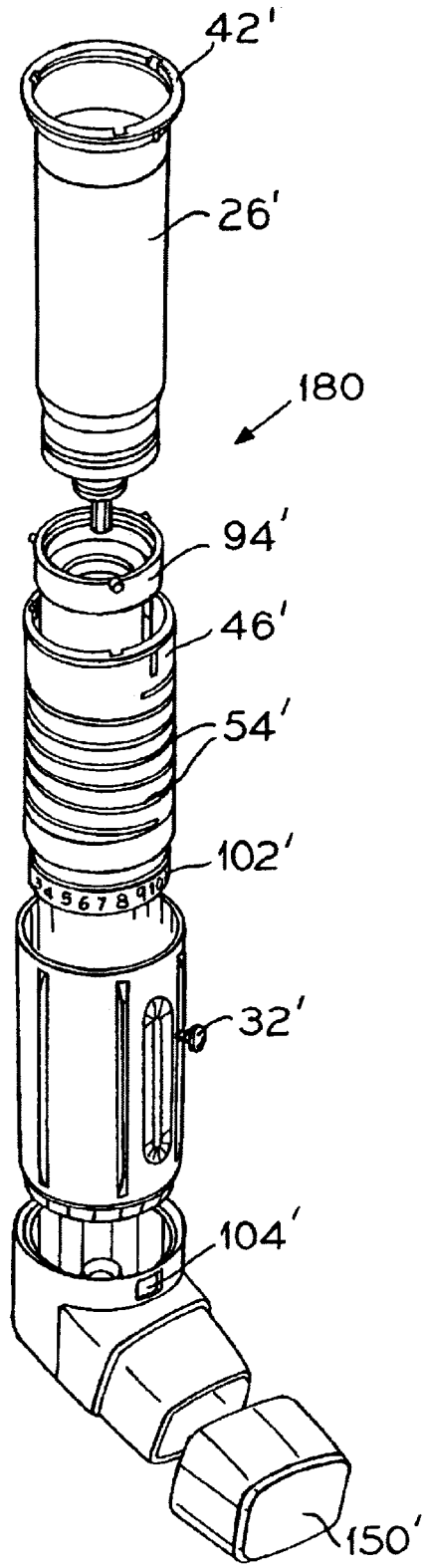
FIG. 26 is an exploded view of the FIG. 25 embodiment.

The manner in which the serrated groove 98 functions is illustrated in FIG. 23 where the circles in and along the track defined by groove 98 represent progressive positions of one of the three stud or pin members 96 that radially upwardly project from the advance ring 94 and that are engaged with the groove 98 in the assembled and operating embodiment 10. In FIG. 23, the arrow A indicates the direction of rotation of advance tube 46, the arrows B1 and B2 indicate, respectively, the downwards longitudinal movement, followed by the upwards longitudinal movement of the advance ring 94 with stud members 96, and the curved arrows C indicate the path of travel of stud member 96 in groove 98 during longitudinal movements of the advance ring 94. As indicated in FIG. 23, the illustrative stud member 96 is in position A when the advance ring 94 is in its resting state (or rest position). The resting state exists when no compressive force is being applied to the exposed distal end of the dispenser 26 that is associated with the device 10. In this state, the dispenser 26 valve is in a fully closed and non-operating configuration in the dispenser 26. The advance ring 94, as explained, is associated with the proximal end of the dispenser 26.

When the exposed distal end of the dispenser 26 is axially compressed by a user, the dispenser 26 body moves longitudinally and downwardly relative to the housing 12 towards the nozzle 14. When the applied compressing force is sufficient to actuate the dispenser 26 valve, the result is that a predetermined medication dose is dispensed from the dispenser 26 and exits the device 10 through the nozzle 14. During the longitudinal downward movement of the dispenser 26, the advance ring 94, which is associated with the dispenser 26 as explained, together with the stud members 96, concurrently also move longitudinally and downwardly towards the nozzle 14. The stud member 96 illustrated in FIG. 23 moves from position A to position B within the serrated groove 98. As stud member 96 moves, it comes into contact with adjacent lower edge portions of the groove 98 and exerts a camming force thereupon which causes the groove 98 to move to the left (in FIG. 23) resulting in the stud member 96 reaching first position C and then position D. Position D corresponds to the location of dispenser 26 where the dispenser valve 26 is fully open and a medication dose is dispensed.

Thereafter, the applied compression force against the distal end of the dispenser 26 is released, and the spring means (not shown) inside the dispenser 26 valve acts to return the dispenser 26 in a longitudinal direction relative to the housing 12 to its rest position (or resting state). Concurrently, as shown in FIG. 23, the stud member 96 moves from position D to position E where the stud member 96 comes into contact with adjacent side edge portions of the groove 98 where a camming force causes the groove 98 to the left (in FIG. 23) and thereby concurrently cause the advance tube 46 to rotate to the left. The stud member 96 moves to position F and then back to a position A2 which corresponds to the rest position (or resting state) of the dispenser 26. Position A2 is a position in groove 98 that is in circumferentially spaced relationship to the groove 98 position that is position A.

The configuration of the groove 98 with its offset opposite side edge configuration and dimensions guides the stud members 96 and allows the advance tube 46 to rotate in only one direction and prohibits the advance tube 46 from backing up or counter rotating. The groove 98 in cooperation with the stud members 96 thus achieve a critical function in the device 10. The advance tube 46 is rotated in incremental steps, so that the helical groove 54 defined in the outer surface 56 of the advance tube 46 advances to a predetermined extent, and so that the level display device 32 advances in the helical groove 54 and in longitudinal slot 34 to a predetermined extent, responsive to each actuation of the dispenser 26 valve. Thus, the level display device 32 accurately measures the number of actuations of the dispenser 26 valve. The number of actuations provide an indication of the quantity of medicament remaining in the dispenser 26 and of the daily (or cumulative) dose received by a user of the device 10. It is important to note that the stud members 96 do not rotate or move along the groove 98, but move only longitudinally and reciprocally. It is the longitudinal and reciprocal motion of the stud members 96 in the groove 98 that forces the advance tube 46 to rotate in one direction.

The dose counter feature of the device 10 is optional but preferred. If desired, this feature need not be included in an embodiment of device 10, as those skilled in the art will readily appreciate. When utilized, the dose counter feature is operated by the same dispenser 26 valve actuations that dispenses a medication dose. As can be appreciated from, for example, FIG. 23, the reciprocal movement of the stud members 96 rotates the advance tube 46. Since the advanced tube 46 here carries both the helical groove 54 and the printed numerical indicia 102, the rotation of the tube 46 provides the needed movement to count both dispenser 26 medicament level and number of doses. Each time the dispenser 26 is depressed and the dispenser 26 valve is actuated, a next succeeding number appears in the window or port 104 of nozzle 14. For a user to count the user's daily dose each day, the dose counter can be reset by the user rotating the nozzle 14 relative to the housing 12 until the number "0" appears in the window 104. Thus, if desired, a user can make a fresh count each day. The device 10 does not permit the dispenser 26 medicament level to be reset, but permits the number of doses to be reset (through rotation of the nozzle 14 relative to the housing 12, as explained).

FIG. 11A depicts an alternate embodiment of the advance tube 46 of FIG. 11. The elements in FIG. 11A designated by reference numerals in the 1000 series, having the last two or three digits in common with elements described above with respect to FIG. 11, correspond to and have similar functions or structure as the elements described above. At least one downwardly, helically extending groove 1054 is defined in the outer surface 1056 of advance tube 1046 and is operably associated with the level display device 1032, the level display device 1032 being illustratively snap-fitted into groove 1054.

However, it is contemplated that medicament in dispenser 26 could be sold in a multiplicity of doses. Typically, the medicament dispenser 26 comes in 100 and 200 doses, although other dose amounts are contemplated. Therefore, it is contemplated that the level indicator device 1032 of the present invention must accommodate such different dose sizes. FIG. 11A depicts an advance tube 1046 able to accommodate dispensers 26 having such different dose size. The helically wound groove 1054 of FIG. 11A has a different angle, linear length and spacing compared to the helically wound groove 54 of FIG. 11. Further, while only one helically wound groove 1054 is shown, two or more grooves, each having a different angle, linear length, and spacing, and each able to accommodate different indicator devices 1032 are contemplated.

FIGS. 13–15 provide further detail on the advance ring 94. FIG. 13 is a top plan view, FIG. 14 is a side elevational view and FIG. 15 is a side elevational view in cross-section of the advance ring 94. In embodiment 10, the advance ring 94 has a generally circular shape when viewed from above, and is preferably made of surgical metal material or rigid plastic suitable for sterilization and reuse or disposal.

As shown in FIGS. 13–15, advance ring 94 is movably disposed in lumen 48 in operable communication with the advance tube 46 that is movably disposed in lumen 20. The advance ring 94 has preferably and as shown three projecting members 96 that extend therefrom, are integral therewith, are disposed in the tube lumen 48 and are operably associated with the serrated groove 98 of the advance tube 46. As shown, at lease one, and often a plurality, but preferably three projection tabs 97 extend outwardly, longitudinally, and upwardly from each member 96. Preferably, the tabs 97 are circumferentially equally spaced and preferably each tab 97 is integrally and centrally (relative to an individual tab 97) associated with a projecting stud member 96. The advance ring 94 further includes a ring base portion 122 defining at least one central aperture 124 therein. While only one aperture 124 is shown, two or more apertures are contemplated depending on the particular medicament dispenser 26.

A peripheral side wall portion 126 is shown extended generally upward from and integral with ring portion 122, so that the inner surface 128 of side wall portion 126 and ring base portion 122 define a cup-like structure (see FIG. 15). Side wall portion 126 runs along and extends upwardly from a peripheral edge 125 of ring base portion 122, although other arrangements are contemplated. For example, wall portion 126 could run along and extend from the inner circumference of the ring portion 122 (around the aperture 124).

Projecting tabs 97 extend upwardly from and are integral with side wall portion 126, while each projecting member 96 extends radially outwardly from and is integral with each tab 97. As shown in FIG. 13, the three projecting members 96 each having a projecting tab 97, are equally spaced about, and project from outer surface 130 at the proximal end 132 of the ring 94. The tabs 97 are believed to improve the capacity to slidably and longitudinally move the ring 94 along the inner surface of the tube 46 when the ring 94 in association with a dispenser 26 is advanced into the tube 46 during assembly of device 10 for use. However, other arrangements are contemplated including having the projecting members 96 attached to any portion of the outer surface 130, including distal end 134, depending on the position of the advancing ring 94 in the lumen 48. Preferably each projecting member 96 of a ring 94 is operably associated with the serrated groove portion 98.

As provided above, device 10 includes a dose indicator device. The advance tube 46 includes indicia 102 disposed thereon (see FIGS. 9 and 11) and visible through the display port 104 defined in nozzle 12 (see FIGS. 16–18). The indicia 102 illustratively comprise a series of numbers that are imprinted on a strip of paper that is attached to the tube distal end 100, and each number indicates a number of doses. The display port 104 is defined in the upper portion 36 of the nozzle 12 in fluid communication with the nozzle lumen 74 and is in spaced and positional relationship with the advance ring 94. As the advance tube 46 rotates, the numbers of the indicia 102 are displayed through the display port 104 in sequence. While a strip of paper is used in one embodiment, other indicia devices for displaying the number of doses are contemplated. For example, the numbers could be written or printed directly upon the tube distal end 100. Furthermore, projecting members 96 could operably engage a counting device connected to an analog or digital display for displaying the number of doses administered.

Figure 16:
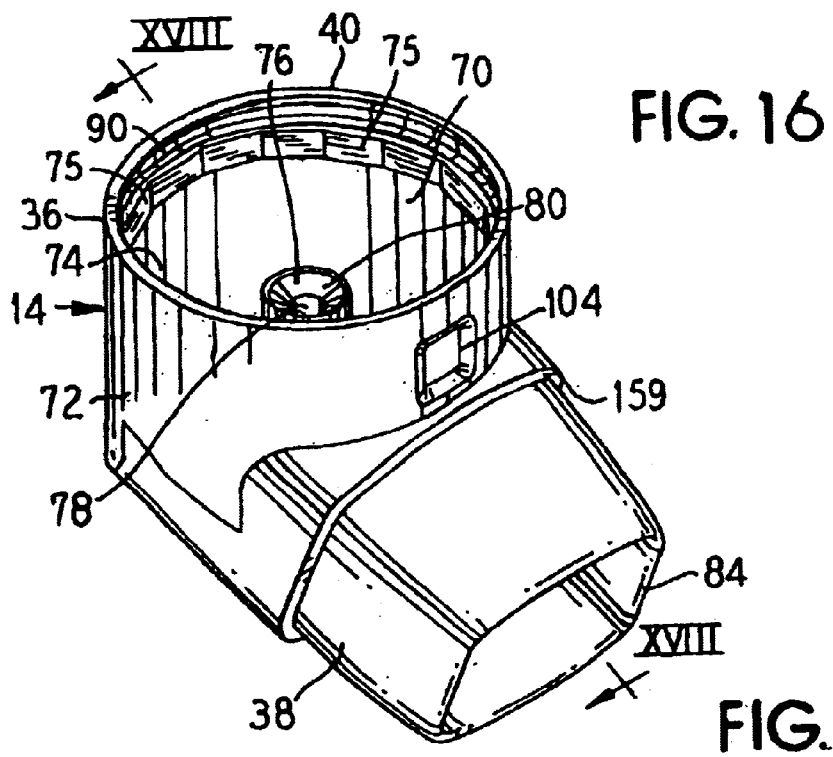
FIG. 16 is a perspective view of the nozzle of the FIG. 1 embodiment removed from the housing and other components.
Figure 17:
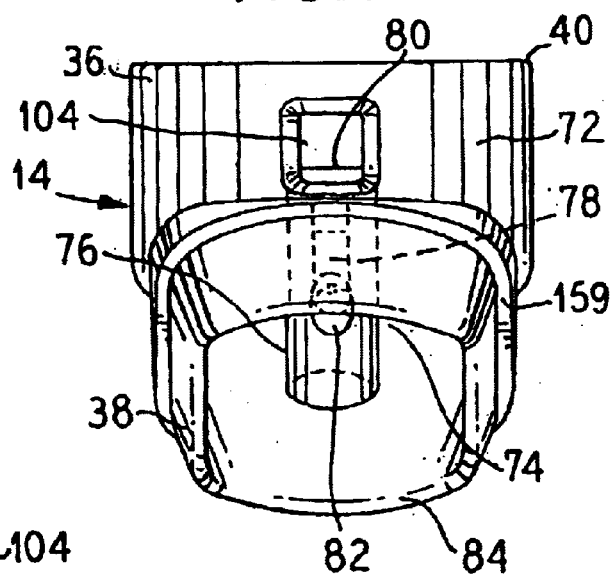
FIG. 17 is a front elevational view of the nozzle of FIG. 16.
Figure 18:
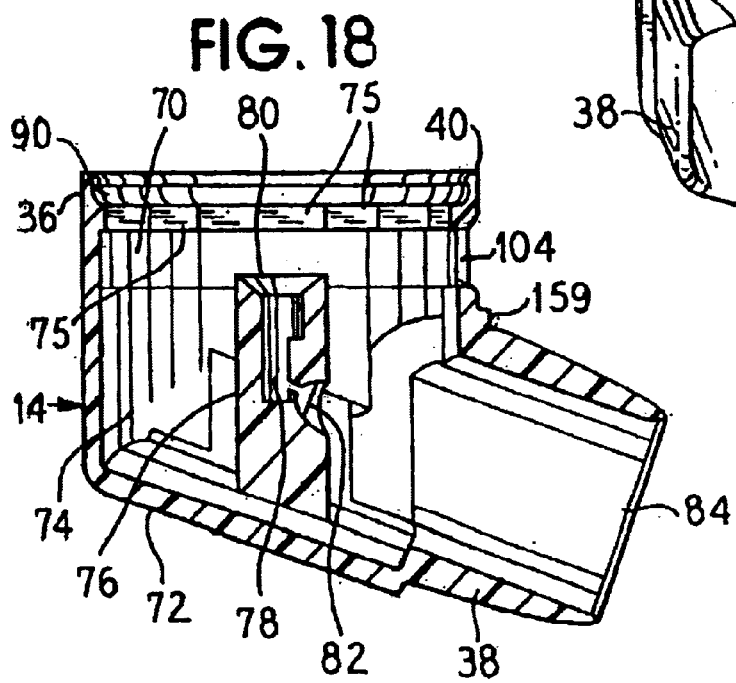
FIG. 18 is a longitudinal cross sectional view of the FIG. 16 nozzle taken substantially along the line XVII—XVII of FIG. 16.

FIG. 1 illustrates that nozzle 14 is intended for insertion into the mouth of a user, although it is contemplated that inhalation device 10 could be used with any orifice of the body. FIGS. 16–18 illustrate further detail on nozzle 14. FIG. 16 shows a perspective view of the nozzle 14 removed from the housing 12, while FIGS. 17 and 18 show a front elevational and side elevational view in cross-section. It is preferred that nozzle 14 be comprised of surgical metal material or rigid plastic.

FIG. 19 shows a side elevation view of the level display device 32 which preferably includes a pointer 136 comprised of surgical metal material or rigid plastic. Pointer 136 here includes a rounded upper portion 138, which is generally circular when viewed from the front, and a post member 140, which extends therefrom and is integral therewith. While a circular shape is shown, other shapes are contemplated including, for example, diamonds and arrows. Pointer 136 further includes at least one flange or lip 142 projecting generally radially outwardly from post member 140 and extending around the circumference thereof. While one lip 142 is shown, two or more lips 142 or even a plurality of generally radially outwardly extending nubs are contemplated.

As shown, post member 140 has a predetermined outer circumference such that a distal end 144 can extend through the slot 34 and operably engage helically extending groove 54 about tube 46. Lip 142 is positionally spaced from the upper portion 138 so that the pointer 136 can slidably move in slot 34 in a linearly reciprocal fashion. Lip 142 is further formed having angled and engaging surfaces 146 and 148. Angled surface 146 is formed so that it can readily pass through the slot 34 into the lumen 20 where an engaging surface 148 on lip 142 then slidingly engages inner surface 18 of the housing 12.

When advance tube 46 is inserted into the lumen 20, the pointer 136 is inserted through the slot 34 to operably engage the helically wound groove 54. Lip 142 is sufficiently flexible to pass through the slot 34. Pointer 136 is advanced through the slot 34 until the distal end 144 operably engages the helically wound groove 54 in a snap-fit fashion so that the engaging surface 148 engages the inner surface 18. The interaction of distal end 144 with the helically wound groove 54 and engaging surface 148 with the inner surface 18 are sufficient to hold the pointer 136 in place in slot 34. As the advance tube 46 advances and moves rotationally in lumen 20, the operable association of the distal end 144 and the helically wound groove 54 causes the pointer 136 to slidably move in the slot 34 in a linear fashion. This movement of the pointer 136 is indicative of the amount of medicament remaining in the medicament dispenser 26. As shown in FIGS. 1 and 5, the slots 34 include markings or mountings 33 which assist the user in determining how much medicament remains.

FIG. 19A depicts an alternate embodiment of the pointer 136 of FIG. 11. Correspondingly, the last three digits in the 1000 series of numerals depicted in FIG. 19A are connected to elements which have the same function and/or structure as those described with regard to FIG. 19. In FIG. 19A, upper portion 1138 of the level display device 1032, i.e., the pointer 1136, is depicted as a double arrow.

FIGS. 20 and 21 illustrate a replaceable cap 150 for removable and replaceable use with nozzle 14. FIGS. 20 and 21 show a perspective view and side elevational view in cross section of cap 150. It is contemplated that replaceable cap 150 is formed of surgical metal material or rigid plastic suitable for sterilization and reuse or disposal.

In embodiment 10, the replaceable cap 150 has a generally trapezoidal shape when viewed from the end; however, other shapes are contemplated. Replaceable cap 150 is formed so that it engages the distal end of the nozzle 14 at the nozzle opening 84 forming a tight friction fit therewith. A generally flat lid 152 is included in the cap 150 with an integral skirt 154 extending from a peripheral edge 156 thereof. The skirt 154 is further formed with a lower cap edge 158 which abuts against shoulder 159 defined in the nozzle 14.

A chamber 160 is defined in cap 150 by an inner surface 162, while an opening 164 is defined opposite the lid 152 by the lower cap edge 158. At least two lips, first and second lips 166 and 168, project generally inwardly from a lid inner surface 170. While two lips 166 and 168 are shown, three or more lips are contemplated. Furthermore, it is contemplated that replaceable cap 150 could be attached by other means including threads, clasps, pins, etc. In embodiment 10, the opening 164 is configured to receive the distal end of the nozzle 14, with first and second lips 166 and 168 configured to have a tight friction fit with the nozzle outer surface 72.

In operation as a reusable device 10, the medicament dispenser 26 must be inserted into the device 10. In one embodiment, device 10 is disassembled so that the medicament dispenser 26 can be inserted. First, advance tube 46 is removed from the tube lumen 20. This removal requires that the top member 42 be removed from the distal end 24 of housing 12 and the pointer 136 be removed from the slot 34, so that the advance tube 46 containing the advance ring 94 can be removed from the housing 12. Note that concave engaging portion 35 assists the user in removing the pointer 136.

The user can now reassemble the inhalation device 10 to incorporate the medicament dispenser 26, if desired. Medicament dispenser 26 is operably associated with the advance ring 94. This is preferably accomplished by inserting the outlet valve member of the medicament dispenser 26 into the aperture 124 so that the forward or proximal end of the medicament dispenser 26 is in contact with the inner surface 128 and is contained in the cup-like structure defined by the inner surface 128 and the ring portion 122. The medicament dispenser 26 and the advance ring 94 can now be operably associated with the advance tube 46 and the resulting subassembly can be inserted into the proximal end 22 of housing 12.

When the inhalation device 10 is used with medicament dispenser 26, the protruding portion or outlet valve member (not shown) of the medicament dispenser 26 is inserted into first opening 80 and passageway 78, so that the dispenser is supported by the support 76.

Figure 24:
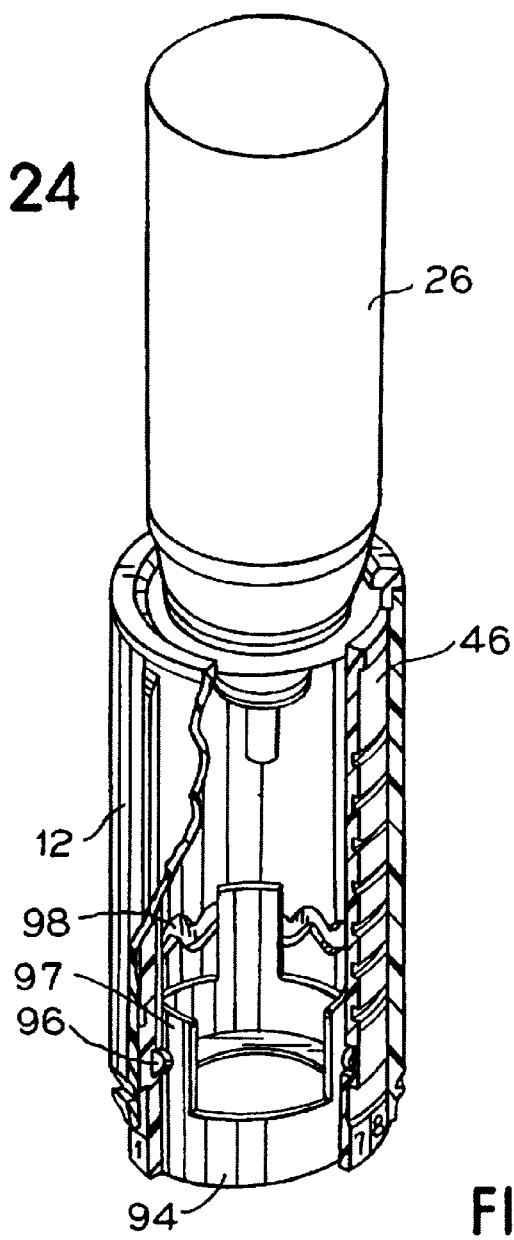
FIG. 24 is a fragmentary exploded view of the assembled combination of the housing, the advance tube and the advance ring with a dispenser being assembled therewith, some parts being broken away and some parts thereof being shown in section.

Alternatively, as shown in FIG. 24, the advance tube 46 and the advance ring 94 can be preliminarily assembled with the housing 12 and then the dispenser 26 can be inserted into the lumen 48 of the advance tube 46 to the longitudinal extent needed to associate fully the dispenser 26 proximal end and associated dispenser 26 valve with the advance ring 94.

It is also contemplated that the inhaler device 10 is disposable, wherein the device 10 is sold with the dispenser 26 already disposed therein and with advance ring 94 fixedly connected to dispenser 26.

It is contemplated that, after usage of a dispenser 26, advance ring 94 and the associatiated dispenser 26 are removed from tube lumen 48. In this application, a fresh medicament dispenser 26 and associated advance ring 94 are inserted into the tube lumen 48. As shown in FIGS. 9 and 10, three grooves 58 are defined in and equally spaced about the inner surface 60 partially along the longitudinal axis of the advance tube 46. The advance ring 94, preferably including the medicament dispenser 26, is placed in the tube lumen 48 so that the projecting members 96 of the ring 94 each operably engage a different groove 58 initially. Each projecting member 96 is preferably in spaced adjacent relationship to the associated groove 58, so that the advance ring 94 slidably advances in the tube lumen 48 in a linear fashion until the projecting members 96 operably engage the serrated portion 98.

When the level display device 32 is in place, the top member 42 may be associated with housing 12 as above described.

Preferably advance tube 46, which is rotatably disposed within the tube lumen 48, has the projecting members 96 of the ring 94 operably engaging the teeth 118 of the serrated groove portion 98. Downward pressure on the advance ring 94 causes the three projecting tabs 97 to move into, and press downwardly on, the grooves 120 defined in the serrated portion 98 by teeth 118. Releasing the pressure on the advance ring 94 causes the projecting tabs 97 to move towards the tip of the next tooth and groove in the series of teeth 118 and grooves 120, in a rachet-like fashion. Furthermore, as the three projecting tabs 97 engage the grooves 120, it causes the advance tube 46 to rotate in the lumen 20.

As the advance tube 48 advances and moves rotationally in the lumen 20, the operable association of the distal end 144 and the helically wound groove 54 causes the pointer 136 to slidably move in the slot 34 in a linear fashion. This movement of the pointer 136 is indicative of the amount of medicament remaining in the medicament dispenser 26. Further, as the advance tube 46 rotates, the indicia device 102 rotates, indicating the number of doses administered during a predetermined period. At the end of such period, nozzle 14 can be rotated until the first number, preferably 0, is visible in display port 104. This acts to reset the dose indicator device.

After all the medicament is dispensed from the dispenser 26, the dispenser 26 may be removed from tube lumen 48 and discarded, if device 10 is reusable. However, it is also contemplated that device 10 is disposable, wherein both the dispenser 26, housing 12, nozzle 14 and cap 150 are discarded. The level indicator device 30 may be reset by rotating advance tube 46 in the counter-advance direction, i.e., opposite to that of the normal advance rotation. In turn, this will cause the level display device 32 to return to its original position in slot 34 in a linear fashion. The inhalation device 10 is now ready for reuse.

FIGS. 25–29 show an alternative embodiment of the inventive inhalation device generally designated as 180. Device 180 is generally similar to device 10 in structure and operation, and similar components are correspondingly similarly numbered but with the addition of prime marks thereto for convenient identification purposes.

In device 180, the unitarily formed advance ring 94' has three equally circumferentially spaced projecting stud members 96' that each radially outwardly extend from a position adjacent to the outer open edge of the side wall 126' thereof. To accommodate the stud members 96' in the lumen 48' of the advance tube 46' during assembly and disassembly of the device 180, three equally circumferentially spaced, longitudinal grooves 58' are defined in the inner surface 60' of the advance tube 46' that each extend from the upper proximal end 108' of tube 46' to the serrated groove 98'.

Alternatively, if desired, three such grooves (not shown) could be defined in the inner surface 60' of the advance tube 46' that each extend from the lower distal end 110' of the tube 46' to the serrated grove 98. In this arrangement, during association of a dispenser 26' with the device 180, the proximal end of a dispenser 26' is extended into the lumen 48' of the advance tube 46' and engaged with the advance ring 94' after the advance ring 94' has been associated with the advance ring 46' by inserting the advance ring 94' into the advance tube 46' through the distal end 110' of advance tube 46'.

In device 180, the advance tube 46' is unitarily molded of a sterilizable plastic (preferred) or metal.

Figure 25:
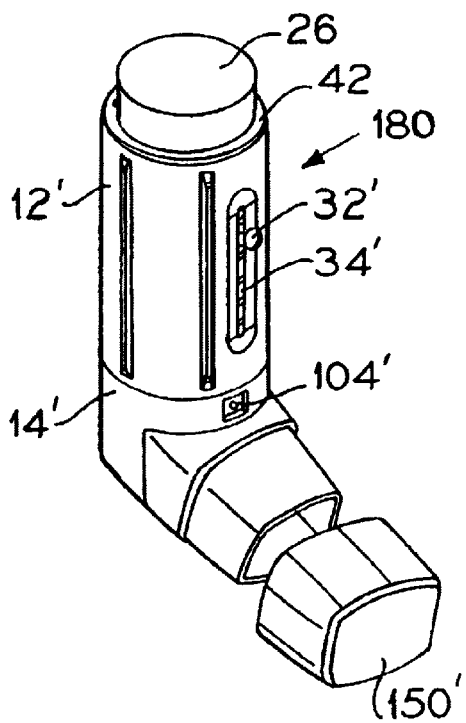
FIG. 25 is a perspective view of another embodiment of the inventive inhalation device which is similar to the FIG. 1.
Figure 25A:
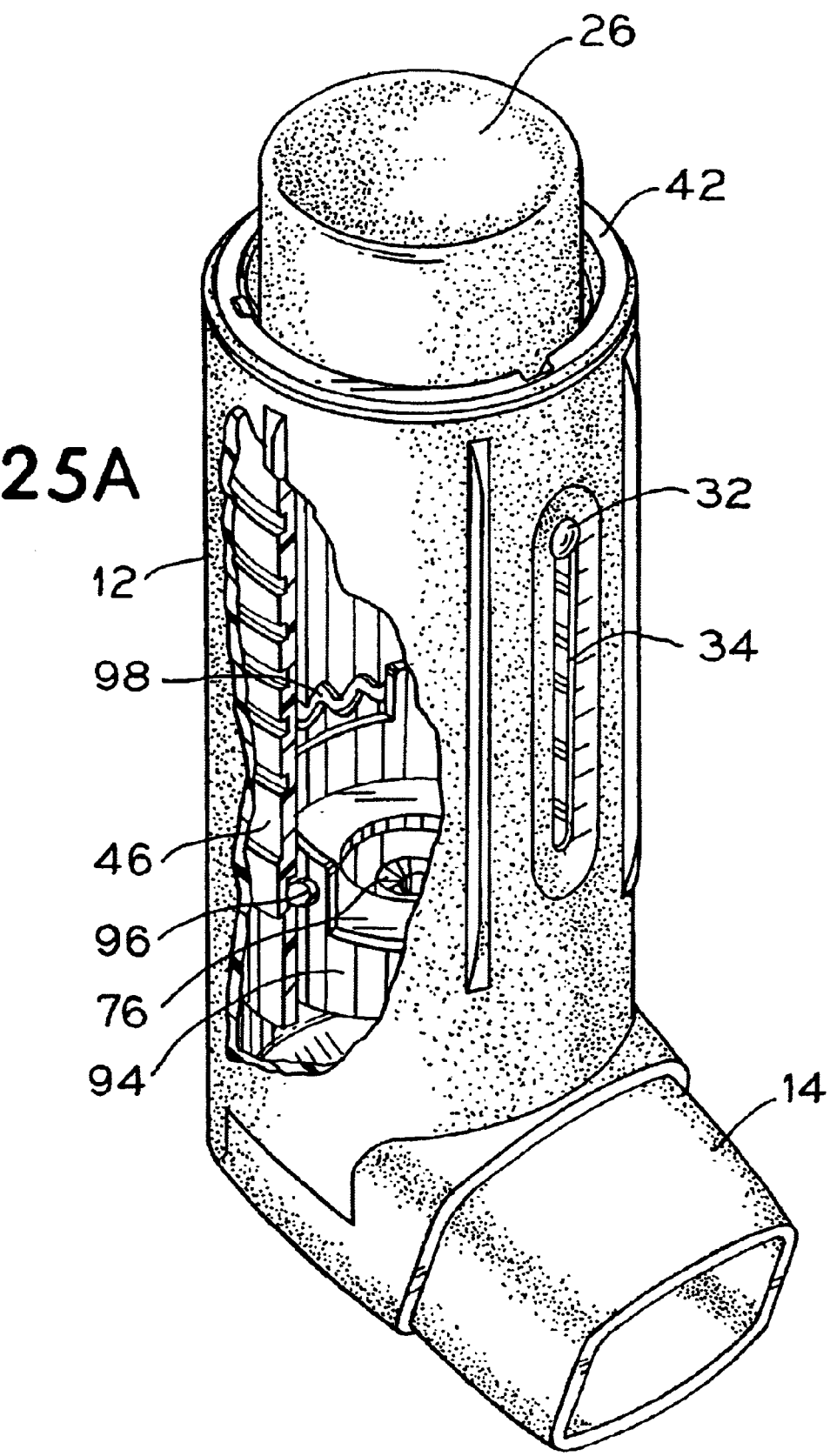
FIG. 25A is a perspective view of another embodiment of the inventive inhalation device, some parts thereof being broken away, and some parts thereof being shown in section.
Figure 27:
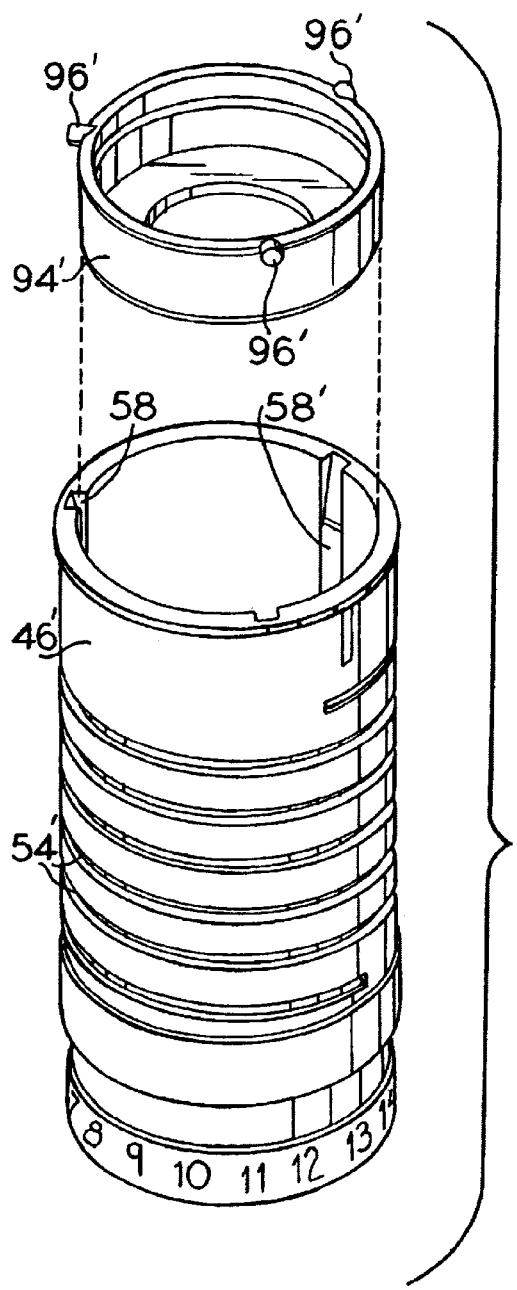
FIG. 27 is an exploded view of the advance tube and advance ring of the FIG. 25 embodiment.
Figure 28:
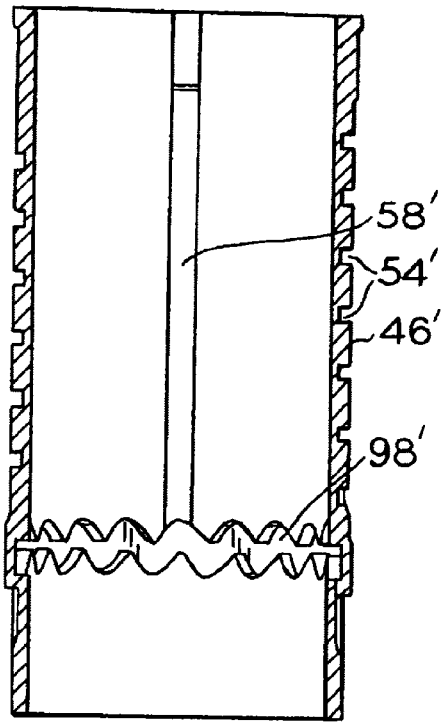
FIG. 28 is a longitudinal cross sectional view of the advance tube of the FIG. 25 embodiment.
Figure 29:
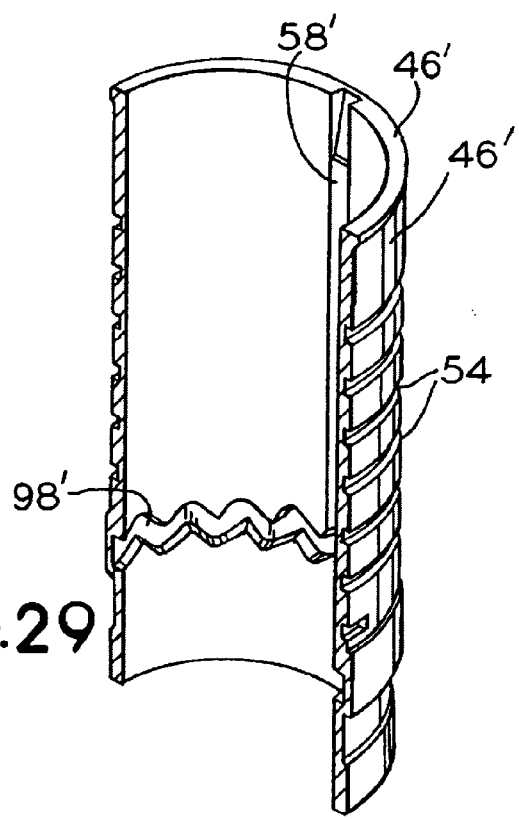
FIG. 29 is a perspective view of the advance tube as sectionally shown in FIG. 28.

If desired, an inhalation counter device can be provided, as indicated above, which does not incorporate a dose counter. Such a device can also be prepared with a nozzle fixed to the housing. An illustration of such a device is provided in FIG. 25A. Here, a housing 12' and a nozzle 14' are each separately formed by molding plastic or the like and then are bonded together by an adhesive (not shown), sonic welding, or the like. By appropriate sizing of housing 12' and nozzle 14', the advance ring 94, the advance tube 46, the top member 42, and the level display device 32 of embodiment 10, illustratively, are associated with the housing 12', and the dispenser 26 is associated with the assembled structure as shown in FIG. 25A. The lower end of the advance tube 46 is not provided with numerical indicia, and no window in the nozzle 14' is provided.

In a device 10 or 180, the advance ring 94 or 94' is reasonably stable and resistant to rotational movement relative to the advance tube 46 or 46' when the valve of the associated dispenser 26 or 26' is actuated. However, study indicates that when the advance ring 94 or 94' is longitudinally and reciprocatingly moved, as explained, and the advance tube 46 or 46' is rotatably moved by the camming action of the stud members 96 or 96' upon edge portions of the serrated grove 98, as also previously explained, it may under certain conditions be possible for slight rotational movements of the advance ring 94 or 94' to occur. Such a movement, if it occurred, could interfere with, or detract from, the accuracy of medicament amount and dose number provided through usage of a device 10 or 180. Hence, for reasons of safety and of achieving maximum possible accuracy in the indicated amount of medicament in a dispenser 26 or 26' by a device 10 or 180, and also in the indicated number of doses dispensed by using a device 10 or 180, it would be desirable to prevent the advance ring 94 or 94' from experiencing any rotation in a device 10 or 180. At the same time, there should be no interference with the longitudinal reciprocal movability of the advance ring 94 or 94' relative to housing 12 or 12' and advance tube 46 or 46'.

To achieve this desirable result, in the present invention, keying means is provided for interlocking an advance ring, such as advance ring 94 or 94', with a housing, such as housing 12 or 12', in an inhalation device, such as device 10 or device 180.

Various illustrative embodiments of such keying means are provided. For present descriptive and illustrative purposes, the keying means is preferably incorporated into an inhalation device that is similar to embodiment 10 except that certain changes, as now described, which are introduced into the housing 12 and the advance ring 94, as illustrated in embodiments of FIGS. 30 and 30A, 31 and 31A, and 32.

In the embodiments of each of FIGS. 30 and 30A, 31 and 31A, and 32, the housing 12 at its distal end 24 is provided with a plurality of circumferentially preferably equally spaced, rearwardly projecting legs 201. The legs 201 are radially inwardly spaced relative to the outer surface 16 of housing 12 so as to avoid interference with the above described arrangements for associating the nozzle 14 with the housing 12. Also, while the respective lengths of the legs 201 are equal to one another, these lengths are such that no interference occurs between the legs 201 and portions of the nozzle 14.

The legs 201 at their respective ends are associated with a flattened disk-202 that has a central aperture 203 defined therein. The size and shape of the aperture 203 are such that the support 76 in the nozzle 14 can extend upwardly therethrough when the nozzle 14 is in connected association with the housing 12.

In each of the embodiments shown in FIGS. 30 and 30A, 31 and 31A, and 32, the advance ring 94 is provided with a pair of flanges 204 that are integrally formed with the ring portion 122 and that project rearwardly therefrom. Relative to the ring portion 122, the flanges 204 are each of generally uniform thickness, and each extends arcuately and in adjacent relationship to the aperture 124 defined in ring portion 122. The flanges 204 are in opposed but inversely curved relationship to each other on opposite side of the aperture 124.

Figure 30:
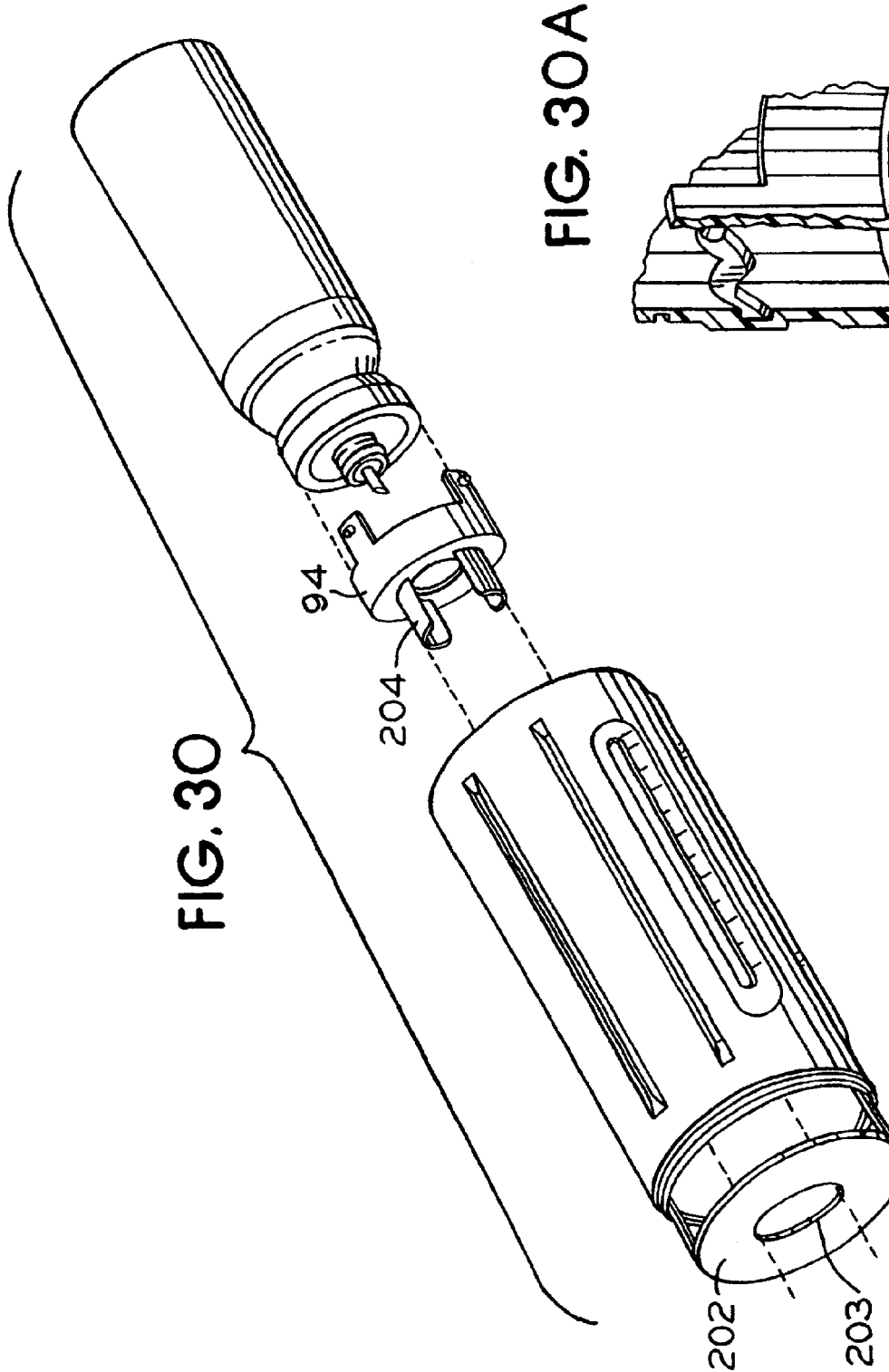
FIG. 30 is a partially exploded, perspective view of an alternative embodiment of the FIG. 1 type wherein the advance ring is keyed to an extended lower portion of the housing.

In the embodiment shown in FIGS. 30 and 30A, terminal outside end edge portions of each flange 204 are configured for facilitating entrance into the aperture 203 when the advance ring 94 is slidably and longitudinally moved through the lumen 48 of the advance tube 46 during assembly of the device 10 and association thereof with a dispenser 26.

To aid in this assembly, conveniently and preferably the advance ring 94 is preliminarily associated with the proximal end region of the dispenser 26. Conveniently and preferably, there is a dissociatable friction fit between this proximal end region and the advance ring 94, thereby to reduce the possibility that the advance ring 94 could dissociate from the dispenser 26 as the subassembly of advance ring 94 and dispenser 26 is slidably extended through the lumen 48 beginning at the proximal end 22 of housing 12.

During assembly, when the flanges 204 reach the disk 202, they pass through the aperture 203 into full engagement with the disk 202 without interference with the support 76. Outside surface portions of the flanges 204 frictionally engage adjacent portions of the aperture 203 so that the flanges 204, and thereby the advance ring 96, are restrained from rotational movement relative to the aperture 203. However, the interrelationship between the flanges 204 and the aperture 203 is such that the flanges 204 are longitudinally and reciprocally moveable relative to the aperture 203 when the dispenser 26 is compressed relative to housing 12 and the dispenser 26 valve is actuated followed by release of the compression force, as explained previously.

Figure 31:
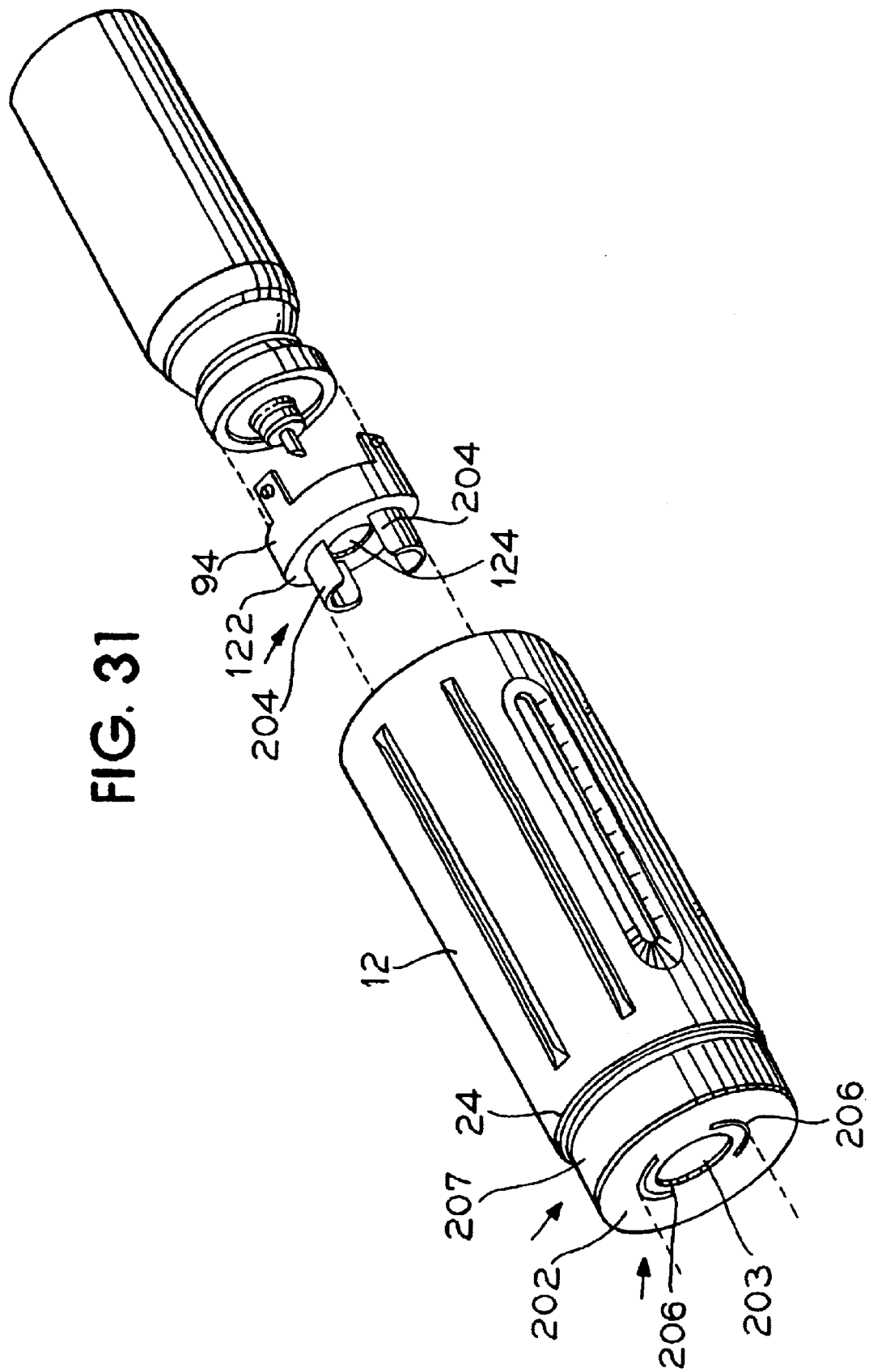
FIG. 31 is a view similar to FIG. 30, but showing an alternative arrangement for keying the advance ring to an extended portion of the housing.
Figure 31A:
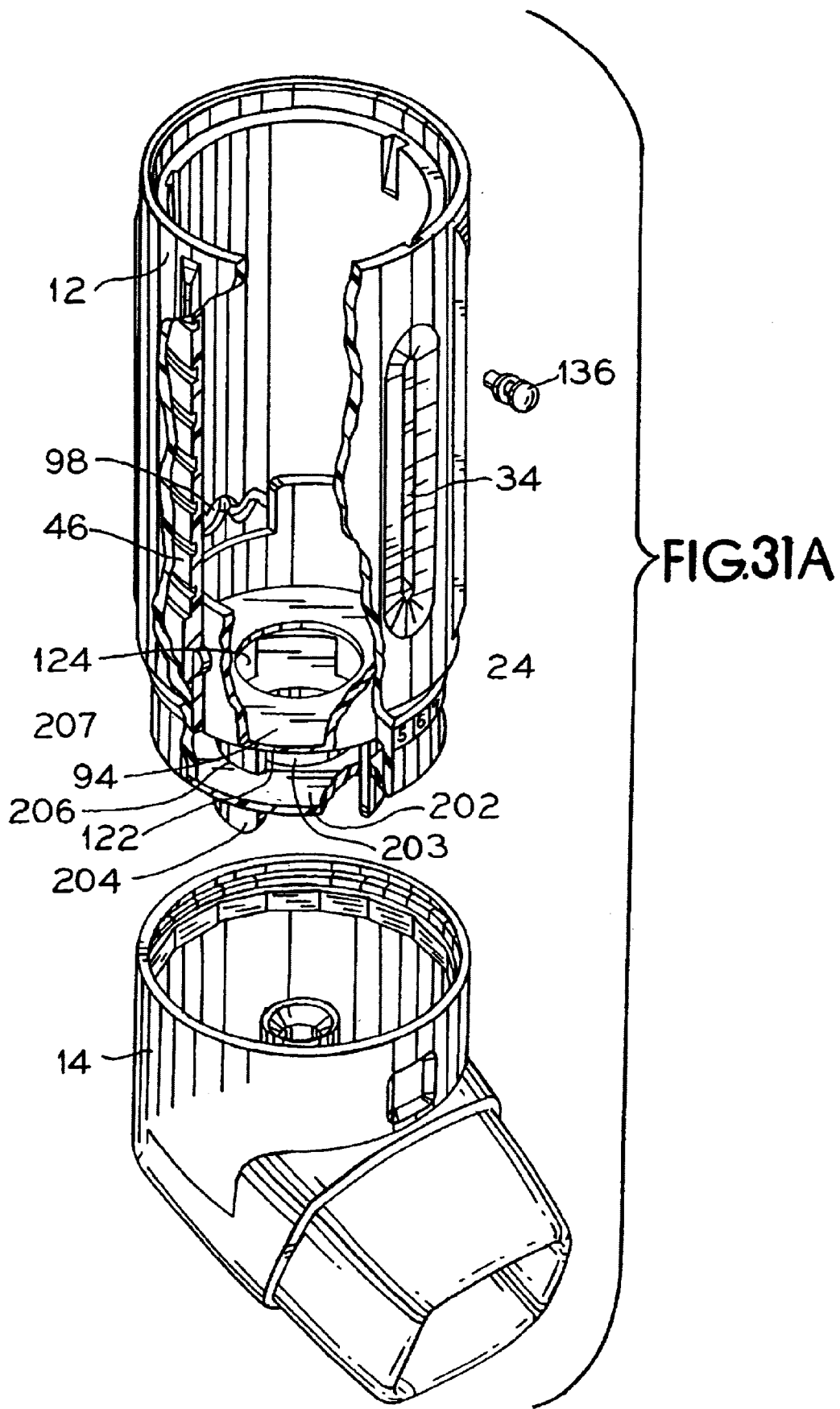
FIG. 31A is an exploded view of the FIG. 31 embodiment, some parts thereof broken away and some parts thereof shown in section.

The embodiment shown in FIGS. 31 and 31A is similar to that shown in FIGS. 30 and 30A, except that, in the FIGS. 31 and 31A embodiment, a pair of separate slots 206 are defined in the disk 202, each slot 206 being configured for receipt and slidable engagement with a different one of the flanges 204 when the flanges 204 are aligned and oriented therewith during assembly. Thus, the slots 206 permit longitudinal movement of the flanges 204 relative thereto, but not rotational movement of the flanges 204, as desired. In addition, in the FIGS. 31 and 31A embodiment, the legs 201 are circumferentially combined and replaced to achieve a continuously circumferentially extending sleeve 207 that is integral with the outer edge portions of the disk 202 and that snap fits into a socket (not detailed) formed in the housing 12 adjacent inner surface 18 at distal end 24.

The embodiment shown in FIG. 32 is similar to that shown in FIGS. 31 and 31A. However, here, opposite side portions of the aperture 203 are provided with flange-receiving side pockets, or cut-outs, 208 that restrain the flanges 204, when engaged therewith, from rotation, but that allow flange 204 reciprocation, as desired. In addition, side edge portions 209 of the advance ring 46 are provided with alternating longitudinally extending ridges and valleys which are adapted to matingly engage inside surface portions of legs 201 that are here circumferentially flattened and that have inside surface portions that are correspondingly configured relative to the edge portions 209 whereby the edge portions 209 are engageable therewith, thereby to prevent the advance ring 94 from rotating but not reciprocating relative to housing 12. Here, the relationship between the housing 12, the advance tube 46 (which is not shown in FIGS. 30, 31 and 32) and the advance ring 94 can be such that the ring 94 projects longitudinally down into the region occupied by the legs 201 below the ring 94 and the housing 11.

Figure 33:
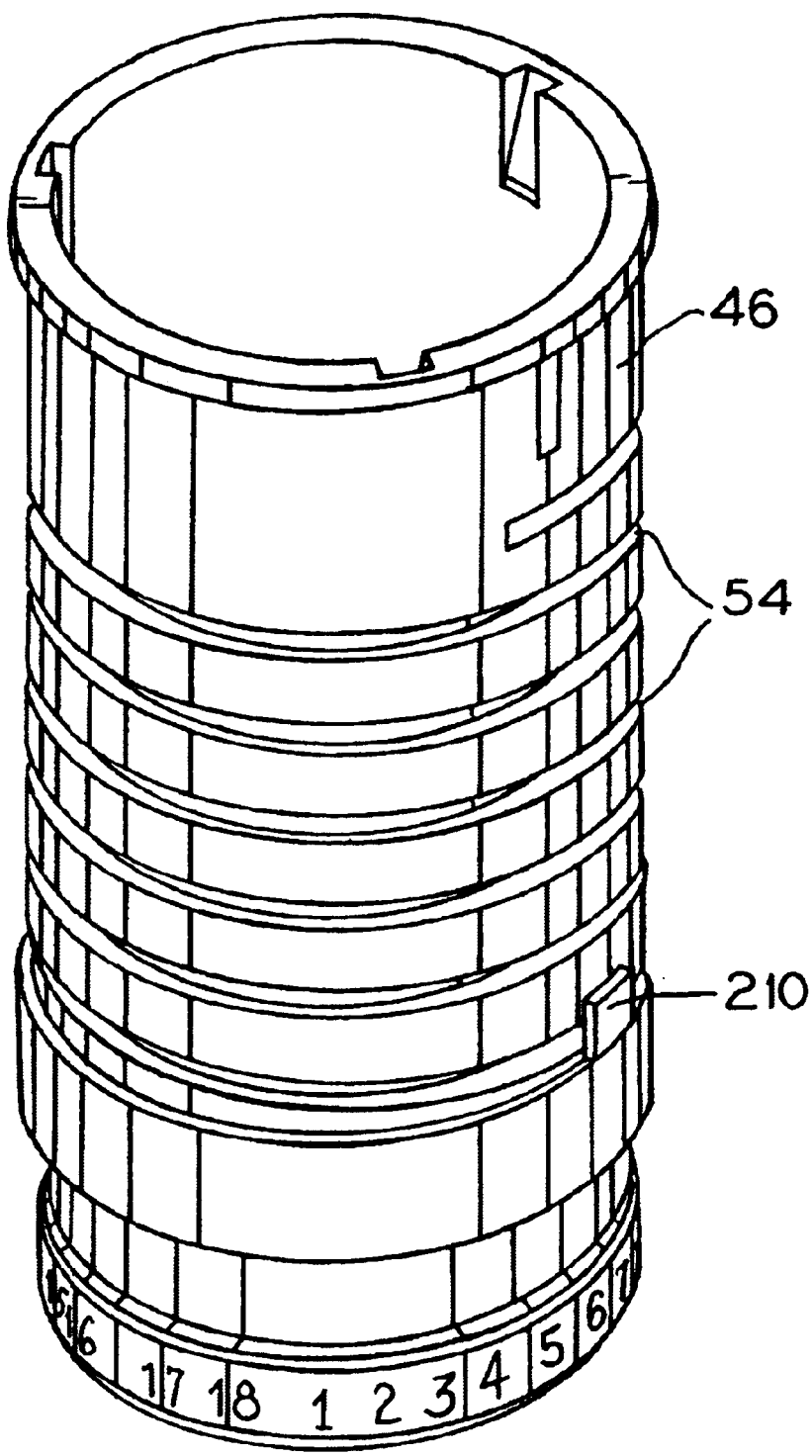
FIG. 33 is a side elevational view of a modified advance tube for the FIG. 1 device embodiment, this advance tube being equipped with a stop that limits further rotational movement of the advance tube.
Figure 34:
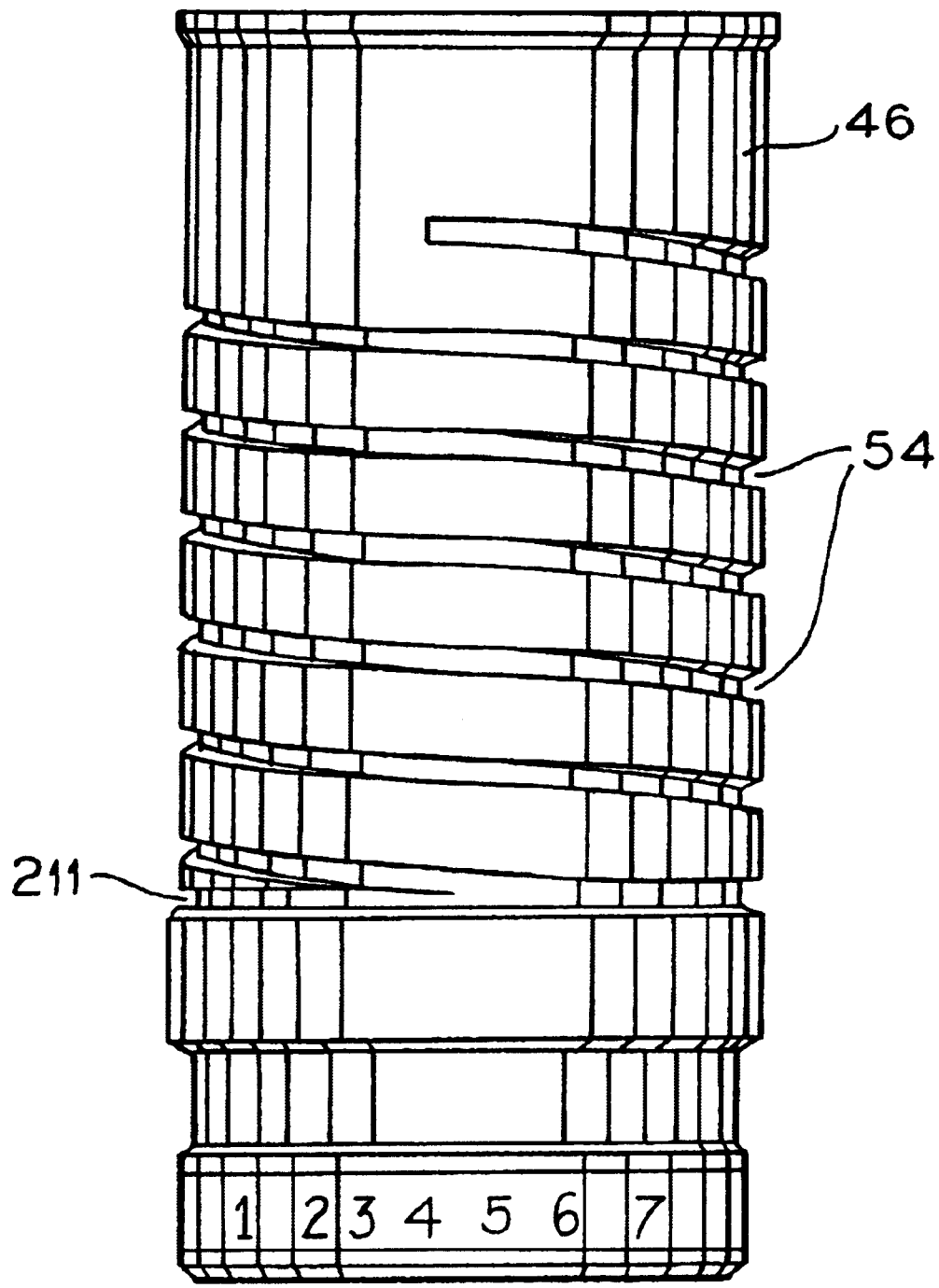
FIG. 34 is a view similar to FIG. 33 showing another modified advance tube for the FIG. 1 device embodiment, this advance tube being equipped with an endless loop at the termination the helical groove.

When in use a device 10 reaches the state where the level display device 32 has advanced to, or nearly to, the lower end of the slot 34, it is desirable to have the device 10 perform in a predictable manner. Two possible modes of operation are illustrated in FIGS. 33 and 34, respectively, and now described. In the presently improved inhalation device, improvements are provided which optionally can be used and which are adapted to achieve such operational modes. Each can be used if desired to regulate movement of the advance tube 46 or 46' when the tube 46 or 46' has been advanced to an extent that the level display device 32 is at, or is approaching, the lower end of the longitudinal slot 34 in housing 12.

In one embodiment of the inhalation device 10, a "lock-out" mechanism is provided, such as illustrated in FIG. 33, that prevents the inhalation device from operating. The "lock-out" mechanism is simply and effectively achieved by placing an impediment or stop 210 at the terminus of the helical groove 54 of the advance tube 46. The stop 210 has a lump configuration, such as shown in FIG. 33. When the level display device 32 (not shown in FIG. 33) has advanced (as a result of use of the device 10) to the stop 210, further rotational movement of the advance tube 46 is prevented. Also, movement of studs 96 in groove 98 is prevented, and longitudinal movement of the dispenser 26 is prevented so that medication cannot be dispensed.

In another embodiment of the inhalation device, shown illustratively in FIG. 34, the advance tube 46 is allowed to rotate after the level indicator device 32 has advanced to about the bottom of the longitudinal slot or groove 54. Here, the helical groove 54 in the advance tube 46 at the groove 54 terminus is formed into a circular (or endless) groove 211. When the tube 46 is rotatably advanced in device 10 operation, the groove 211 allows medication to be dispensed from the dispenser 26 (to the extent that any medicament remains in the dispenser 26), yet does not allow the level indicator device 32 (not shown in FIG. 34) to move further down in the slot 34. The groove 211 allows the advance tube 46 to rotate responsive to camming action exerted in the serrated groove 98 by the stud members 96 while the level indicator device 32 remains on "empty" at the bottom of the slot 34.

In another improvement, as illustrated in FIGS. 35–38, a nozzle 14' is provided with a "quick disconnect" arrangement for dissociation of the nozzle 14' from the housing 12. This feature is desirable for a patient who needs or desires to clean, perhaps periodically, the interior of the nozzle 14' followed by re-connection of the nozzle 14 with the housing 12. Since the circularly arranged sequential numerical legend 102 remains undisturbed at the distal end of the advance tube 46, no interference results from such a removal and replacement of the nozzle 14'. The "quick disconnect" nozzle 14' is achieved by placing on each opposite side of the nozzle 14' adjacent to proximal end 40' thereof a radially compressible latch arm 212. Each arm 212 is provided at its upper terminal open end with an out-turned flange 213. Opposite sides of each arm 212 are defined by circumferentially spaced longitudinal slots in the body of the nozzle 14'. The lower end of the arm 212 remains integrally associated with the nozzle 14 body and acts as a spring that retains the associated arm 212 in a yieldingly biased upstanding orientation. Between the nozzle 14' at the distal end 24 of the housing 12 is a sleeve 214 whose upper rim is adapted to snap fit about the distal end 24. The lower rim of the sleeve 214 is adapted to seat about a lip defined about the upper or proximal end 40' of the nozzle 14'. Opposite side portions of the lower rim of sleeve 214 each have a slot 215 defined therein that is adapted to receive a different flange 213. Thus, when the latch arms 212 are compressed inwards between a thumb and forefinger, the nozzle 14 is seated against the lower end of the sleeve 214. When the latch arms 212 are released, the flanges 213 seat in the slots 215 so that the nozzle 14 is held against the adjacent end of the sleeve 214. A reverse procedure disengages the nozzle 14 from the sleeve 214. The sleeve 214 is provided with a window 104 which is aligned with the numerical indicia 102 when the assembled device 10 is assembled with the nozzle 14'.

In another improvement, also illustrated in FIGS. 35–38, the nozzle 14' is provided with a nozzle stand 217 that is unitarily formed with the nozzle 14 body by molding or the like. The nozzle stand 217 has a bottom configuration that enables the stand 217 to support relative to an underlying flat surface the device 10 in an upright orientation.

FIG. 39 illustrates a modified device 10' wherein the sleeve 214 is eliminated, the slots 215 are placed adjacent the distal end 24' of the housing 12', and the nozzle 14' directly connects to the distal end 24'. The component sizes and proportions are such that the window 104' is here in the housing 12'.

Figure 41:
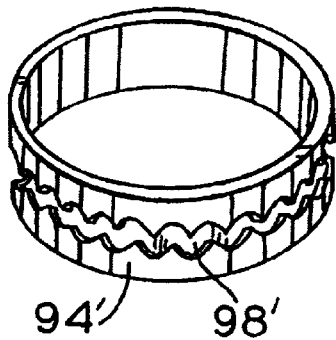
FIG. 41 is a perspective view of the advance ring of the FIG. 40 embodiment.
Figure 42:
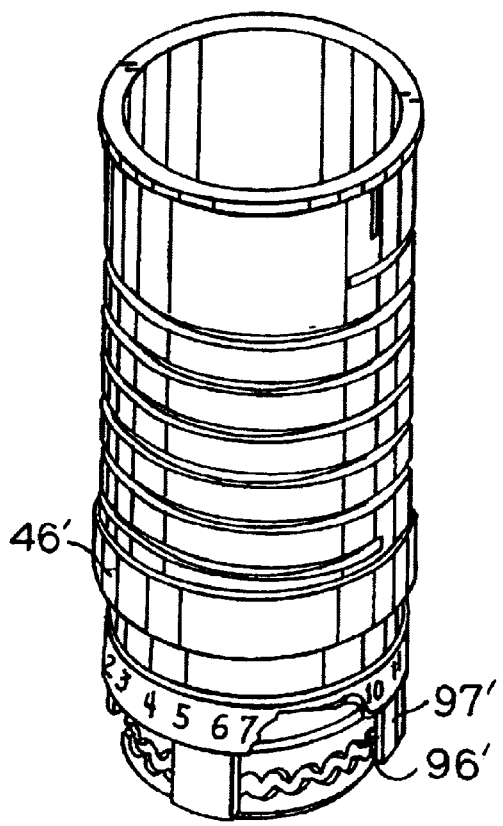
FIG. 42 is a perspective view of the advance tube of the FIG. 40 embodiment shown in combination with the FIG. 40 advance ring, some parts thereof being broken away.
Figure 40:
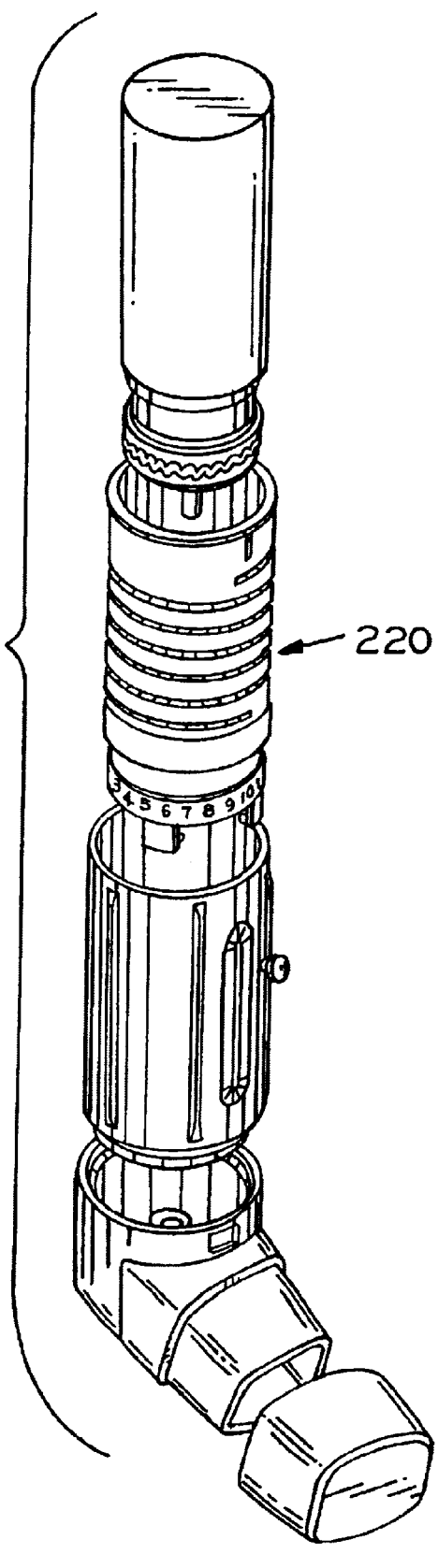
FIG. 40 is an exploded perspective view of an alternative embodiment of an inventive inhalation device.
Figure 49:
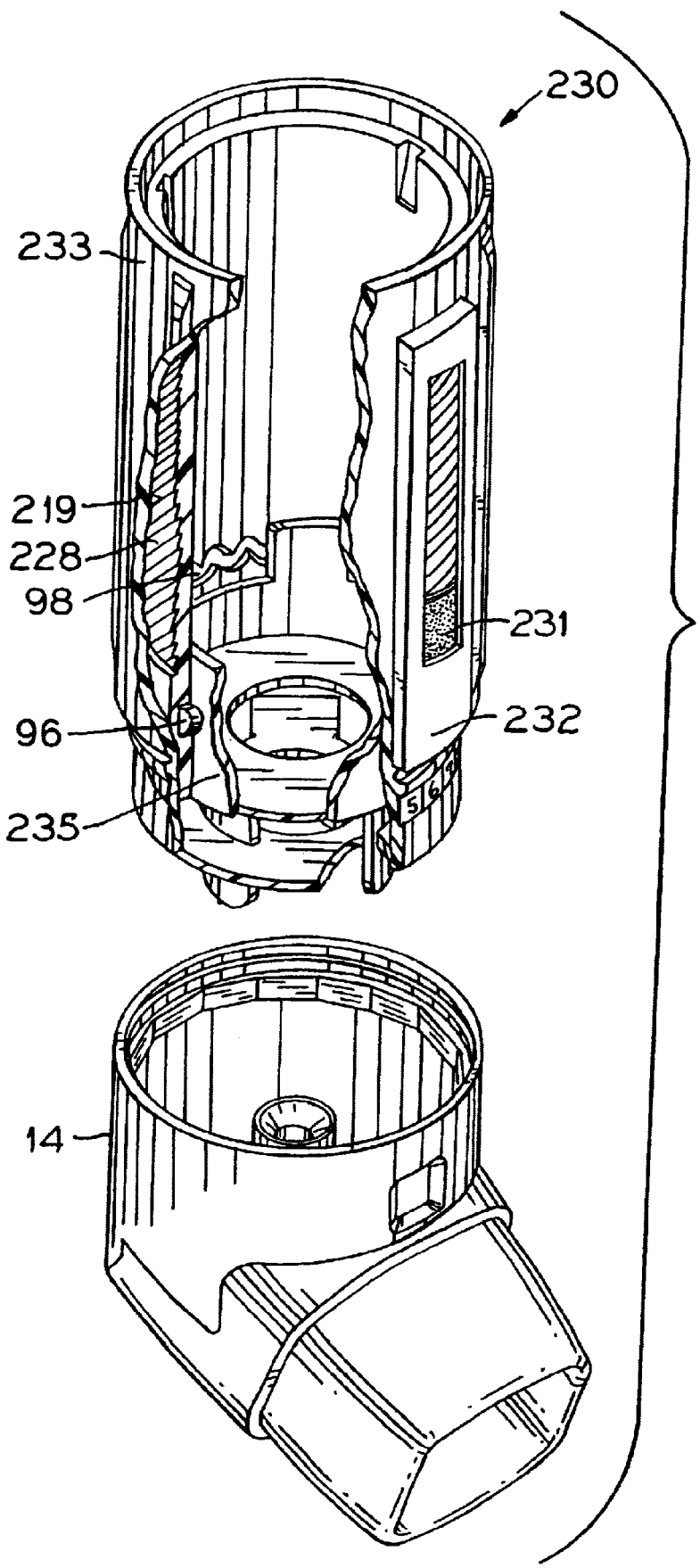
FIG. 49 is an exploded view of an alternative embodiment, some parts thereof broken away and some parts thereof shown in section.
Figure 50:
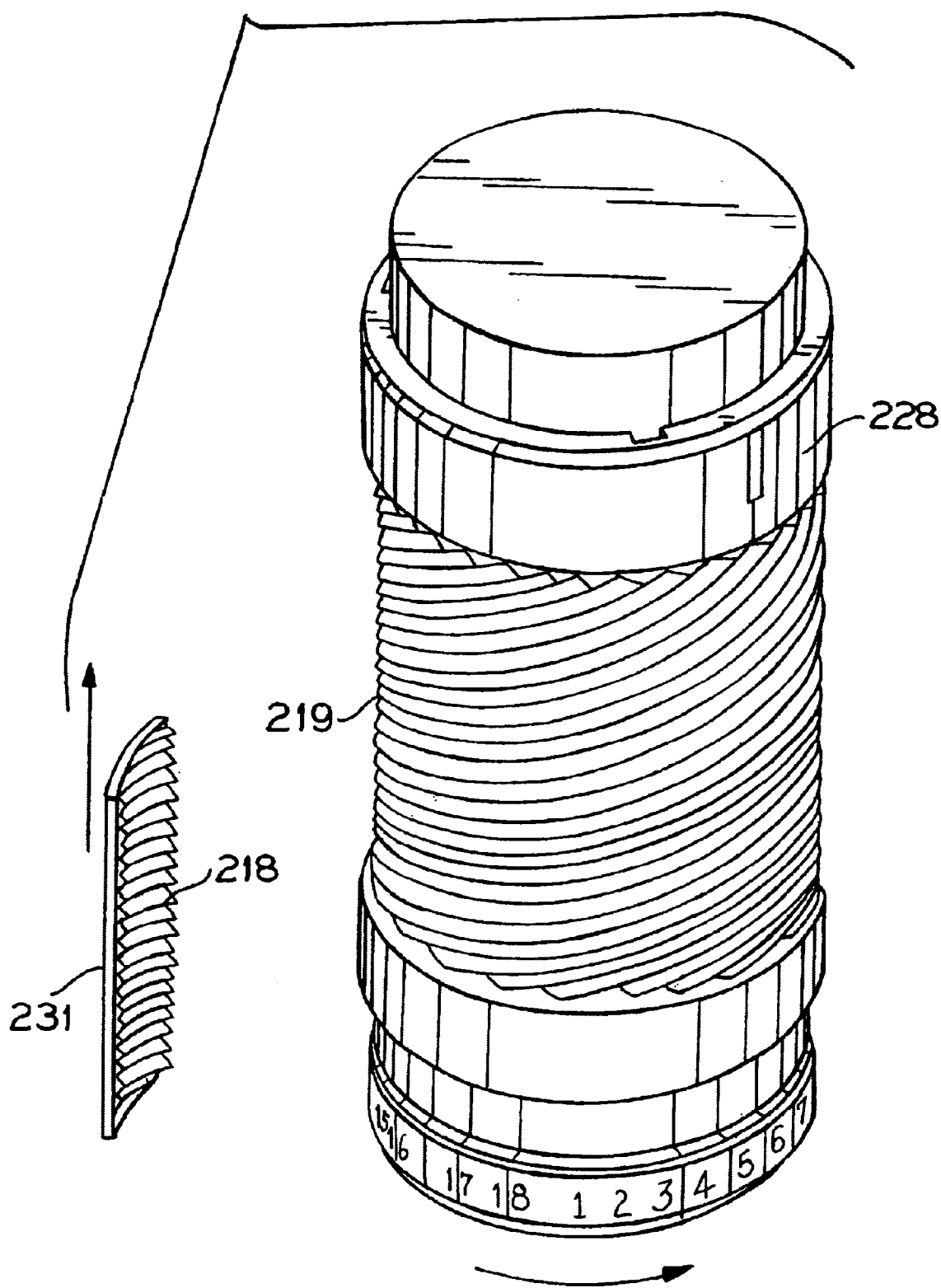
FIG. 50 is a perspective view of the advance tube and the level indicator leaf employed in the FIG. 49 embodiment.

FIGS. 40–42 illustrate an alternative embodiment 220 of an inhalation device of the invention wherein the groove 98 and the studs 96 are interchanged with one another so that the groove 98' is here on the advance ring 94' while the studs 96' are here on the tabs 97' that downwardly extend from the advance tube 46'. In this device 220, the serrated groove 98' is relocated about the circumference of the advance ring 94' while the projecting stud members 96' are relocated on the bottom of the advance tube 46'. Other components are as indicated relative to embodiment 10. The advance tube 46' and the advance ring 94' of embodiment 220 are relatively easier to mold unitarily compared to the advance tube 46 and the advance ring 94.

FIGS. 43–48 illustrate an alternative embodiment 221 of an inhalation device of the invention. Here, the groove 98' on the advance ring 94' of embodiment 220 is replaced by a zigzag raised ridge or rail 222 that circumferentially extends about the outside of an advance ring 94" and the studs 96' on the advance tube 46' of the embodiment 220 are replaced by at least one pair of longitudinally spaced, adjacent guidance skids 224 on the tabs 226 of the advance tube 46". The skids 224 each ride on a different generally opposed side edge portion of the rail 222 so that, as the advance ring 94" reciprocally moves longitudinally during actuations of the dispenser 26 valve, the skids 224 cam against the rail 222 and cause the rail 222 to move rotatably. Owing the configuration of the rail 222, which corresponds to the configuration of the groove 98 (above explained), the tube 46" rotatably advances in one direction only.

FIGS. 49–52 illustrate an alternative embodiment 230 of an inhalation device of the present invention. In device 230, the helical groove 54 of advance tube 46 is replaced by threads 219, that are formed preferably by molding or the like, about exterior portions of an advance tube 228. These threads 219 engage another set of threads 218 that are molded into an inside face of a level indicating leaf 231. In the assembled and operating embodiment 230, the threads 218 engage the threads 219, and the level indicating leaf 231 is carried in a longitudinally extending leaf housing 232 that is provided on the outside of the device housing 233 and that extends over the longitudinal slot 234 in housing 233. The serrated advancing groove 98 (not shown in FIGS. 49–52) cooperate with the advance ring 235 with stud members 96 and operate as in device 10. Except for the threads 219 and 218, the operation of the embodiment 230 may be regarded as being is similar to the components and operation of the embodiment of FIGS. 31 and 31A where that advance ring 94 is provided with guidance flanges 204. The illustrative arrangement of the threads 219 and 218 is such that, as the arrows shown in FIG. 50 indicate, as the advance tube 228 rotates responsive to reciprocal movements of advance ring 235 during operation of the embodiment 230, the leaf 231 rises in housing 232 along slot 234. The locations of the threads 218 and 219 and their respective associated components can vary, if desired, depending upon needs and objectives.

FIGS. 53–55 illustrate an alternative embodiment 175 of the inventive inhalation device wherein the zigzag groove (which, as above described in associated with either the advance ring or the advance tube) is replaced with a functionally equivalent structure while the usually cylindrical sided stud (or pin) member (which as above described in association with correspondingly either the advance tube or the advance ring) is replaced with another functionally equivalent structure.

Thus, in FIG. 53, a suitable zigzag track 176 is defined by a combination of projecting posts 177 and projecting diamonds 178. A plurality of the posts 177, each substantially identical to the others, are each circumferentially located relative to the other posts 177, and each is in circumferentially equally spaced relationship relative to the other posts 177, and each radially outwardly upstands (relative to the outer or inner associated cylindrically curved surface advance ring or advance tube, as the case may be for a particular embodiment). Here, illustratively, each post 177 is associated with an advance tube 179. Each post 177 has a pointed head 182 that is identical to the head 182 of the other posts 177. Each head 182 is defined by symmetrical, lateral, straight head sides 183 that taper from a post's opposite sides 184 to the post's head 182. The post heads 182 here point downwards and meet at and along a common circumference (called for convenience the "post circumference").

A plurality of diamonds 178, each substantially identical to the other diamonds 178, are each circumferentially located relative to the other diamonds 178, and each is in circumferentially equally spaced relationship relative to the other diamonds 178, and each radially outwardly upstands (relative to the outer or inner associated cylindrically curved surface, as the case may be for a particular embodiment). Here, illustratively, the diamonds 178 are associated with the advance tube 179. Each diamond 178 has equal sides, and each diamond 178 has a perimeter configuration that is identical to that of the other diamonds 178, and the diamonds 178 are arranged so that two corners of each diamond fall along a common circumference (called for convenience the "diamond circumference").

The "diamond circumference" is longitudinally spaced from the "post circumference" in an assembled and operating embodiment. However, the posts 177 are circumferentially offset relative to the diamonds 178 so that together the posts 177 and the diamonds 178 define therebetween a zigzag track that can be considered to be somewhat similar to the zigzag track illustrated, for example, in FIG. 23.

At least one, and preferably a plurality of, hexagonally sided stud or pin members 187 outstand from the other of the advance tube or the advance ring; here, illustratively the advance ring 186. Each hexagonally sided stud member 187 is similar to the others thereof, and each is here considered illustratively to be longitudinally symmetrical relative to its respective left and right sides. While opposite sides 188 and 189 of each stud member 187 extend parallel to each other, one opposite side 188 is longer than the other side 189. The respective pair members of adjacent sides 190 and 191, relative to each of the opposite sides 188, 189, respectively, are symmetrical and equal in length to each other. However, the adjacent sides 190 of the longer one 188 of the opposite sides 188, 189 are shorter than the adjacent sides 191 of the shorter one 188 of the opposite sides causing the respective pairs of adjacent sides 190, 191 to intersect off center relative to the associated stud 187.

When the advance ring 186 and the advance tube 179 are functionally engaged in the embodiment 175, the size and orientation relationships between the studs 187 and the combination of diamonds 178 and posts 177 is such that the studs 187 are slidably moveable between adjacent pairs of diamonds 178, adjacent pairs of posts 177, and adjacent pairs of diamonds 178 and posts 177. When the advance ring 186 is longitudinally moved responsive to an actuating end-applied force against the distal end of a dispenser, each of the involved hexagonally shaped studs 187 advances along the zigzag track defined by the posts 177 and diamonds 178.

In FIG. 53, the arrow A indicates the direction of rotation of advance tube 179, the arrows B1 and B2 indicate, respectively, the downwards longitudinal movement, followed by the upwards longitudinal movement of the advance ring 186 with stud members 187, and the various arrows C indicate the path of travel of stud members 187 in and along the path defined by the posts 177 and the diamonds 178 during longitudinal movements of the advance ring 186. From an initial or rest position between a pair of circumferentially adjacent posts 177, an hexagonally shaped stud 187 moves downwards (as shown in FIG. 53 from position A to position B, where the stud 187 comes into contact with a diamond 178. At this location, the stud 187 cams against the side of the diamond 178 and in effect, as the advance tube 179 rotates responsively, moves to position C, and then travels to position D which is between two circumferentially adjacent diamonds 178. Position D is the position where the dispenser's valve is fully compressed and medication is dispensed. When the applied force on the dispenser is released, the stud 187 moves upward from position D and comes into contact with the head 182 region of a post 177. Because of the offset relationship between the posts 177 and the diamonds 178, the stud 187 moves to position E and then to position F which is between an adjacent pair of posts 177 (relative to the starting pair of posts 177). The advance tube 179, because of the indicated offset relationship between posts 177 and diamonds 178, can rotatably move in only one direction.

Although the invention has been described with reference to certain preferred embodiments, numerous modifications and variations can be made by those skilled in the art without departing from the novel spirit and scope of this invention.

What is claimed is:

1. An inhalation device for dispensing a medicament from a dispenser that has an axially disposed, compression actuated, dose metering valve at a proximal end thereof, said device comprising:

(a) a combination of a cylindrical housing and a nozzle body at one housing end, said combination having an internal seat for said valve that is located generally adjacent said nozzle, and having a longitudinal slot in said housing;

(b) a cylindrical advance tube in which said dispenser is slidably receivable and that is slidably engageable with said housing, that has helically extending thread means defined exteriorly therein;

(c) a circular advance ring which is associatable with said dispenser about said proximal end and that is slidably engageable with said advance tube;

(d) one of either said advance tube or said advance ring having a circumferentially extending zigzag track defined therein and the other of said advance tube or said advance ring having at least one radially outwardly projecting stud member defined therein that slidably engages said track when said advance ring is so engaged with said advance tube and with said dispenser; and (e) a level indicator that is slidably engageable with said longitudinal slot and also with said thread means through said longitudinal slot;

the interrelationship between (a), (b), (c), (d) and (e) being such that, when said advance ring moves longitudinally and reciprocatingly when said valve is actuated, said stud member exerts a camming action upon said zigzag track whereby said advance tube rotates and said level indicator advances along said longitudinal slot.

2. An inhalation device for dispensing a medicament from a dispenser that has an axially disposed, compression actuated, dose metering valve at a proximal end thereof, said device comprising:
  (a) a combination of a cylindrical housing and a nozzle body at one housing end, said combination having an internal seat for said valve that is located generally adjacent said nozzle, and having a longitudinal slot in said housing;
  (b) a cylindrical advance tube in which said dispenser is slidably receivable and that is slidably engageable with said housing, that has a helically extending groove defined exteriorly therein, and that has a circumferentially extending zigzag track defined interiorly therein which is located in upwardly spaced relationship relative to said seat;
  (c) a circular advance ring which is associatable with said dispenser about said proximal end and that is slidably engagable with said advance tube and has at least one radially outwardly projecting stud member that is slidably engageable with said track when said advance ring is so engaged with said advance tube and with said dispenser; and
  (d) a level indicator that is slidably engageable with said longitudinal slot and also with said groove through said longitudinal slot;
  the interrelationship between (a), (b), (c) and (d) being such that, when said advance ring moves longitudinally and reciprocatingly when said valve is actuated, said stud member exerts a camming action upon said zigzag track whereby said advance tube rotates and said level indicator advances in said longitudinal slot.

3. An inhalation device for dispensing a medicament from a dispenser that has an axially disposed, compression actuated, dose metering valve at a proximal end thereof, said device comprising:
  (a) a combination of a cylindrical housing and a nozzle body at one housing end, said combination having an internal seat for said valve that is located generally adjacent said nozzle, and having a longitudinal slot in said housing;
  (b) a cylindrical advance tube in which said dispenser is slidably receivable and that is slidably engageable with said housing, that has at least one radially inwardly projecting stud member, and that has a helically extending groove defined exteriorly therein;
  (c) a circular advance ring which is associatable with said dispenser about said proximal end and that is slidably engagable with said advance tube and has a circumferentially extending zigzag track defined exteriorly therein that is slidably engageable with said track when said advance ring is so engaged with said advance tube and with said dispenser; and
  (d) a level indicator that is slidably engageable with said longitudinal slot and also with said groove through said longitudinal slot;
  the interrelationship between (a), (b), (c) and (d) being such that, when said advance ring moves longitudinally and reciprocatingly when said valve is actuated, said stud member exerts a camming action upon said zigzag track whereby said advance tube rotates and said level indicator advances in said longitudinal slot.

4. An inhalation device for dispensing a medicament from a dispenser that has an axially disposed, compression actuated, dose metering valve at a proximal end thereof, said device comprising:
  (a) a combination of a cylindrical housing and a nozzle body at one housing end, said combination having an internal seat for said valve that is located generally adjacent said nozzle, and having a longitudinal slot in said housing;
  (b) a cylindrical advance tube in which said dispenser is slidably receivable and that is slidably engageable with said housing, that has helically extending thread means defined exteriorly therein, and that has a circumferentially extending zigzag track defined interiorly therein which is located in upwardly spaced relationship relative to said seat;
  (c) a circular advance ring which is associatable with said dispenser about said proximal end and that is slidably engagable with said advance tube and has at least one radially outwardly projecting stud member that is slidably engageable with said track when said advance ring is so engaged with said advance tube and with said dispenser; and
  (d) a level indicator that is slidably engageable with said longitudinal slot and also with said thread means through said longitudinal slot, and that includes guidance means along said longitudinal slot for said level indicator;
  the interrelationship between (a), (b), (c) and (d) being such that, when said advance ring moves longitudinally and reciprocatingly when said valve is actuated, said stud member exerts a camming action upon said zigzag track whereby said advance tube rotates and said level indicator advances along said longitudinal slot.

5. An inhalation device for dispensing a medicament from a cylindrical aerosol dispenser that has a proximal end and a distal end, that has a compression actuated, dose metering valve axially disposed in a constricted neck at said proximal end, and said valve includes an axially projecting stem tube through which a single dose of said medicament is dispensed in response to each actuating compression of said valve, said device comprising:
  (a) a generally cylindrical housing having an upper housing end, a lower housing end, a housing side wall defining generally opposed interior and exterior housing side surface portions, and a longitudinally extending slot defined through said housing side wall;
  (b) an L-shaped nozzle body having an input end and an output end, said input end being associated with said lower housing end, and said nozzle body further having an internal central valve seat located in recessed relationship relative to said input end, and an associated internal passageway extending between said valve seat and a terminus located in recessed relationship relative to said output end;
  (c) an advance tube having an upper end and a lower end, and an advance tube cylindrical side wall defining generally opposed inside and outside cylindrically extending surface portions, said advance tube outside surface portions being slidably engagable within said interior housing side surface portions, said advance tube outside surface portions having a helically extending groove defined therein, said advance tube inside surface portions being sized to slidably receive therein said dispenser and said advance tube inside surface portions having a circumferentially extending zigzag track defined therein that is located in upwardly spaced adjacent relationship relative to said advance tube lower end;

(d) a level indicator including a foot portion and a pointer portion, said foot portion extending through said longitudinally extending slot and being engageable with said helically extending groove, said level indicator being slidable along said longitudinal slot and also slidable along said helically extending groove;

(e) an advance ring associatable about said constricted neck of said dispenser, said advance ring including at least one radially outwardly projecting stud member, said advance ring being slidably engageable with said inside circumferential surface portions of said advance tube being slidably engagable within said advance tube inside surface portions, and said projecting stud member being engagable with said zigzag track;

(f) the interrelationship between said housing, said advance tube, and said advance ring being such that:

when said dispenser has been inserted through said advance tube, said advance ring has been so associated with said constricted neck, and said valve has been so seated in said valve seat with said stem tube in said passageway, and when a compression force sufficient to actuate said valve is applied to the distal end of said dispenser and is then released, then said advance ring remains circumferentially stationary relative to said housing, but said advance ring moves reciprocatingly and longitudinally, while concurrently said projecting stud member in said zigzag track exerts a camming force against an adjacent contacted edge portions of said zigzag track and said zigzag track advances responsively, whereby said advance tube rotates relative to said housing, and said level indicator slidably advances both circumferentially along said helical extending groove and also vertically along said longitudinally extending slot, so that the position of said level indicator along said longitudinally extending slot advances and thereby indicates the amount of said medicament remaining in, or dispensed from, said dispenser.

6. The inhalation device of claim 5 wherein an end region of said helically extending groove includes stop means preventing further travel of said level indicator.

7. The inhalation divide of claim 5 wherein an end region of said helically extending groove terminates in an endless circular loop means that prevents further travel of said level indicator.

8. The inhalation device of claim 5 wherein said zigzag track has opposed side edge portions, and each side edge portion has circumferentially defined therein teeth and grooves alternately, and said teeth in one side edge portion are circumferentially offset from said teeth in the other side edge portion so that said teeth in one side edge portion are in longitudinally spaced, relationship to said grooves in the other side edge portion and are also slightly circumferentially offset from a transversely aligned relationship whereby said zigzag track can only move relative to said projecting stud member circumferentially in one direction as said advance ring moves longitudinally and reciprocably during actuations of said valve, thereby causing said advance tube to rotate in only one direction.

9. The inhalation device of claim 5 wherein said lower end of said advance tube extends into said L-shaped nozzle body, consecutive numbers are circumferentially marked on said outside cylindrically extending surface portions of said advance tube lower end, and wherein a window is defined through said L-shaped nozzle body in radial alignment with said numbers, the circumferential spacing of said numbers being such that, each time said advance tube rotates responsively to an actuation of said valve, a different one of said number is viewable through said window.

10. The inhalation device of claim 9 wherein said input end of said L-shaped nozzle body is rotatably associated with said lower housing end whereby, when said L-shaped nozzle body is rotated relative to said housing, said number viewable through said window is changes.

11. The inhalation device of claim 10 wherein an inner surface about said input end of said L-shaped nozzle body overlaps an inner surface about said lower housing end, and wherein each said inner surface has defined therein a plurality of flat panels whereby said L-shaped nozzle body is incrementally rotatably adjustable relative to said housing and each incremental adjustment corresponds to a different one of said numbers on said L-shaped nozzle body.

12. The inhalation device of claim 5 wherein said advance ring includes three of said projecting stud members, and said projecting stud members are in circumferentially equally spaced relationship to each other, and each of said projecting stud members is engagable with a different region of said zigzag track.

13. The inhalation device of claim 12 wherein said advance ring further includes three longitudinally upstanding extensions and each of said projecting stud members is associated with a different one of said extensions.

14. The inhalation device of claim 5 wherein said interior housing side surface portions have at least one longitudinally extending groove defined therein, each said longitudinally extending groove extending from a housing end to said zigzag track whereby each said projecting stud member of said advance ring is slidably movable longitudinally therealong to engagement with said zigzag track.

15. The inhalation device of claim 5 wherein said housing includes a ring member which detachably associates with said housing upper end when said dispenser is positioned in said inhalation device.

16. The inhalation device of claim 5 wherein said L-shaped nozzle body includes a cap which detachably associates with said output end.

17. The inhalation device of claim 5 wherein along said longitudinally extending slot indicia are defined that indicate the amount of said medicament remaining in, or dispensed from, said dispenser.

18. The inhalation device of claim 5 wherein said L-shaped nozzle body includes a stand that enables said inhalation device to rest in an upright configuration upon a flattened surface.

19. The inhalation device of claim 5 wherein said L-shaped nozzle body includes means for disconnectably associating said L-shaped nozzle body with said housing.

20. The inhalation device of claim 19 wherein said means for disconnectably associating includes a pair of latch arms that engage said L-shaped nozzle body with said housing, each latch arm is located on a different opposite side portion of said L-shaped nozzle body, each latch arm includes biasing means retaining said latch arm in a normally closed position relative to said housing, each latch arm being openable by applied digital force, and each latch arm including a terminal flange that engages a receiving slot defined in an adjacent portion of said housing when said latch arm is in said normally closed position.

* * * * *